(12) United States Patent
Bush et al.

(10) Patent No.: US 8,748,377 B2
(45) Date of Patent: Jun. 10, 2014

(54) PHARMACEUTICAL COMPOSITIONS

(75) Inventors: Mark A. Bush, Research Triangle Park, NC (US); Murray W. Stewart, King of Prussia, PA (US); Yonghong Yang, King of Prussia, PA (US)

(73) Assignee: GlaxoSmithKline LLC, Philadelphia, PA (US)

( * ) Notice: Subject to any disclaimer, the term of this patent is extended or adjusted under 35 U.S.C. 154(b) by 0 days.

(21) Appl. No.: 13/133,976

(22) PCT Filed: Dec. 10, 2009

(86) PCT No.: PCT/US2009/067469
§ 371 (c)(1),
(2), (4) Date: Jun. 10, 2011

(87) PCT Pub. No.: WO2010/068735
PCT Pub. Date: Jun. 17, 2010

(65) Prior Publication Data
US 2011/0301080 A1    Dec. 8, 2011

Related U.S. Application Data

(60) Provisional application No. 61/121,229, filed on Dec. 10, 2008, provisional application No. 61/150,909, filed on Feb. 9, 2009, provisional application No. 61/163,995, filed on Mar. 27, 2009, provisional application No. 61/238,723, filed on Sep. 1, 2009.

(51) Int. Cl.
*A61P 7/12*    (2006.01)
*A61K 38/00*    (2006.01)
*A61K 38/22*    (2006.01)
*A61K 39/00*    (2006.01)

(52) U.S. Cl.
USPC .............. 514/7.2; 514/6.2; 514/6.9; 514/5.3; 424/185.1

(58) Field of Classification Search
None
See application file for complete search history.

(56) References Cited

U.S. PATENT DOCUMENTS

| 5,512,549 A | 4/1996 | Chen et al. |
| 5,545,618 A | 8/1996 | Buckley et al. |
| 6,277,819 B1 | 8/2001 | Efendic |
| 6,284,725 B1 | 9/2001 | Coolidge et al. |
| 6,329,336 B1 | 12/2001 | Bridon et al. |
| 6,380,357 B2 | 4/2002 | Hermeling et al. |
| 6,706,689 B2 | 3/2004 | Coolidge et al. |
| 6,747,006 B2 | 6/2004 | Efendic |
| 6,875,432 B2 | 4/2005 | Liu et al. |
| 6,894,024 B2 | 5/2005 | Coolidge et al. |
| 7,141,547 B2 * | 11/2006 | Rosen et al. .............. 514/6.9 |
| 7,189,690 B2 | 3/2007 | Rosen et al. |
| 7,238,660 B2 | 7/2007 | Rosen et al. |
| 7,238,667 B2 | 7/2007 | Rosen et al. |
| 7,259,233 B2 | 8/2007 | Dodd et al. |
| 7,271,149 B2 | 9/2007 | Gleasner et al. |
| 7,521,423 B2 | 4/2009 | Young et al. |
| 7,521,424 B2 | 4/2009 | Rosen et al. |
| 7,569,384 B2 | 8/2009 | Rosen et al. |
| 7,671,023 B2 | 3/2010 | Laugero et al. |
| 7,790,681 B2 | 9/2010 | Hathaway et al. |
| 7,888,314 B2 | 2/2011 | Hathaway et al. |
| 8,071,539 B2 | 12/2011 | Rosen et al. |
| 2003/0220255 A1 | 11/2003 | Knudsen et al. |
| 2005/0054570 A1 | 3/2005 | Rosen et al. |
| 2007/0111940 A1 | 5/2007 | Larsen et al. |
| 2007/0128193 A1 | 6/2007 | O'Neil et al. |
| 2008/0200383 A1 * | 8/2008 | Jennings et al. ............... 514/12 |
| 2008/0254087 A1 | 10/2008 | Bush et al. |
| 2008/0300173 A1 | 12/2008 | DeFrees et al. |
| 2009/0215688 A1 | 8/2009 | Knudsen et al. |
| 2009/0325873 A1 | 12/2009 | O'Neil et al. |
| 2010/0009910 A1 | 1/2010 | Bush et al. |
| 2010/0029554 A1 | 2/2010 | Ghosh et al. |
| 2010/0311662 A1 | 12/2010 | Coolidge et al. |
| 2011/0301080 A1 | 12/2011 | Bush et al. |

FOREIGN PATENT DOCUMENTS

| EP | 0 964 692 B1 | 12/1999 |
| EP | 1 330 261 B1 | 7/2003 |
| WO | WO 98/08531 A1 | 3/1998 |
| WO | WO 03/033671 A2 | 4/2003 |
| WO | WO 03/040309 A2 | 5/2003 |
| WO | WO 03/058203 A2 | 7/2003 |
| WO | WO 03/084563 A1 | 10/2003 |
| WO | WO 2004/056313 A2 | 7/2004 |
| WO | WO 2004/056317 A2 | 7/2004 |
| WO | WO 2005/120492 A1 | 12/2005 |
| WO | WO 2006/073890 A2 | 7/2006 |
| WO | WO 2006/110887 A2 | 10/2006 |
| WO | WO 2007/056681 A2 | 5/2007 |

(Continued)

OTHER PUBLICATIONS

Xiao et al. Biological activities of glucagon-like analogues in vitro and in vivo. Biochemistry, 40:2860-2869, 2001.*
Bowie et al. Deciphering the message in protein sequences: tolerance to amino acid substitutions. Science, 1990, 247:1306-1310.*
Chia, et al., "Incretin-Based Therapies in Type 2 Diabetes Mellitus," *J. Clin. Endocrinol. Metab.*, vol. 93, No. 10, pp. 3703-3716 (2008).
U.S. Appl. No. 13/494,253, filed Jun. 12, 2012, Bush, et al. Non-final Office Action dated Nov. 28, 2012.

(Continued)

*Primary Examiner* — Vanessa L Ford
*Assistant Examiner* — Sandra Dillahunt
(74) *Attorney, Agent, or Firm* — Andrea V. Lockenour; William T. Han

(57) ABSTRACT

The present invention provides pharmaceutical compositions comprising at least one polypeptide having GLP-1 activity wherein an effective dose of said pharmaceutical composition comprises 15 mg, 30 mg, 50 mg or 100 mg of said polypeptide having GLP-1 activity. Also provided are methods of administering the pharmaceutical compositions of the invention.

1 Claim, 4 Drawing Sheets

(56) References Cited

FOREIGN PATENT DOCUMENTS

| | | | |
|---|---|---|---|
| WO | WO 2007056681 A2 * | 5/2007 | |
| WO | WO 2007/140284 A2 | 12/2007 | |
| WO | WO 2008/019143 A2 | 2/2008 | |
| WO | WO 2008/033888 A2 | 3/2008 | |
| WO | WO 2010/028846 A1 | 3/2010 | |

OTHER PUBLICATIONS

U.S. Appl. No. 13/494,253, filed Jun. 12, 2012, Response (dated Feb. 28, 2013 to USPTO Non-Final Office Action dated Nov. 28, 2012.

U.S. Appl. No. 12/092,433, filed May 2, 2008, Response (dated May 13, 2011) to USPTO Non-Final Office Action dated Feb. 15, 2011.

U.S. Appl. No. 12/092,433, filed May 2, 2008, USPTO Non-Final Office Action dated Feb. 15, 2011.

U.S. Appl. No. 12/092,433, filed May 2, 2008, Response (dated Dec. 3, 2010) to USPTO Non-Final Office Action dated Sep. 7, 2010.

U.S. Appl. No. 12/092,433, filed May 2, 2008, USPTP Non-Final Office Action dated Sep. 7, 2010.

Ban, et al., "Cardioprotective and vasodilatory actions of glucagon-like peptide 1 receptor are mediated through both glucagon-like peptide 1 receptor-dependent and -independent pathways", Circulation, vol. 117, No. 18, pp. 2340-2350 (2008).

Bose, et al., "Glucagon like peptide-1 is protective against myocardial ischemia/reperfusion injury when given either as a pre-conditioning mimetic or at reperfusion in an isolated rat heart model", Cardiovasc. Drugs Ther., vol. 19, No. 1, pp. 9-11 (2005).

Bose, et al., "Glucagon-like peptide 1 can directly protect the heart against ischemia/reperfusion injury", Diabetes. vol. 54, No. 1, pp. 146-151 (2005).

Bose, et al., "Myocardial ischaemia-reperfusion injury is attenuated by intact glucagon like peptide-1 (GLP-1) in the in vitro rat heart and may involve the p70s6K pathway," Cardiovasc. Drugs Ther., vol. 21, No. 4, pp. 253-256 (2007).

Bowie, et al., Deciphering the Message in Protein Sequences: Tolerances to Amino Acid Substitutions. Science. 247:1306-1310, Mar. 2010.

Chia and Egan, "Incretin-Based Therpaies in Type 2 Diabetes Mellitus" J Clin Endocrinol Metab, 93(10):3703-3716, Oct. 2008.

Fields, et al., "Glucagon-like Peptide-1 and Myocardial Protection: More than Glycemic Control", Clin. Cardiol. vol. 32, No. 5, pp. 236-243 (2009).

Grieve, et al., Emerging cardiovascular actions of the incretin hormone glucagon-like peptide-1: potential therapeutic benefits beyond glycaemic control?, British Journal of Pharmacology, vol. 157, pp. 1340-1351 (2009).

Gros, et al., "Cardiac function in mice lacking the glucagon-like peptide-1 receptor", Endocrinology, vol. 144, No. 6, pp. 2242-2252 (2003).

Halbirk, et al., "Cardiovascular and Metabolic Effects of 48-Hour Glucagon-like Peptide 1 Infusion in Compensated Chronic Heart Failure Patients," Am. J. Physiol. Heart Circ Physiol. (Jan. 15, 2010).

Huisamen, et al., "Signalling pathways activated by glucagon-like peptide-1 (7-36) amide in the rat heart and their role in protection against ischaemia", Cardiovasc. J. Afr., vol. 19, No. 2, pp. 77-83 (2008).

Kavianipour, et al., "Glucagon-like peptide-1 (7-36) amide prevents the accumulation of pyruvate and lactate in the ischemic and non-ischemic porcine myocardium", Peptides, vol. 24, No. 4, pp. 569-578. (2003).

Kim, et al., "Effects of Once-Weekly Dosing of a Long-Acting Release Formulation of IDG/Exenatide on Glucose Control and Body eight in Subjects with Type 2 Diabetes", Diabetes Care in Press, published online Mar. 12, 2007.

Kristensen, et al., "Lack of cardioprotection from subcutaneously and preischemic administered liraglutide in a closed chest porcine ischemia reperfusion model", BMC Cardiovasc Disord., vol. 23;9:31 (2009).

Liu, et al., "Glucagon-like peptide-1 and the exenatide analogue AC3174 improve cardiac function, cardiac remodeling, and survival in rats with chronic heart failure", Cardiovasc. Diabetol., vol. 16, No. 9, p. 76 (2010).

Luque, et al., "Glucagon-like peptide-1 (GLP-1) and glucose metabolism in human myocytes", J. Endocrinol., vol. 173, No. 3, pp. 465-473 (2002).

Mafong, et al., "The Role of Incretins in Cardiovascular Control", Current Hypertension Reports, vol. 11, pp. 18-22 (2009).

Nathanson, et al., "Plasma levels of glucagon like peptide-1 associate with diastolic function in elderly men", Diabet. Med., vol. 28, No. 3, pp. 301-305 (2011).

Nikolaidis, et al., "Active metabolite of GLP-1 mediates myocardial glucose uptake and improves left ventricular performance in conscious dogs with dilated cardiomyopathy", Am. J. Physiol. Heart Circ. Physiol., vol. 289, No. 6, pp. H2401-H2408 (2005).

Nikolaidis, et al., "Effects of glucagon-like peptide-1 in patients with acute myocardial infarction and left ventricular dysfunction after successful reperfusion", Circulation, vol. 109, No. 8, pp. 962-965 (2004).

Nikolaidis, et al., "Recombinant glucagon-like peptide-1 increases myocardial glucose uptake and improves left ventricular performance in conscious dogs with pacing-induced dilated cardiomyopathy", Circulation, vol. 110, No. 8, pp. 955-961 (2004).

Noyan-Ashraf, et al., GLP-1R agonist liraglutide activates cytoprotective pathways and improves outcomes after experimental myocardial infarction in mice, Diabetes, vol. 58, No. 4, pp. 975-983 (2009).

Nyström, et al., The Potential Benefi cial Role of Glucagon-like Peptide-1 in Endothelial Dysfunction and Heart Failure Associated with Insulin Resistance, Horm. Metab. Res., vol. 40, pp. 593-606 (2008).

Ossum, et al., "The cardioprotective and inotropic components of the postconditioning effects of GLP-1 and GLP-1(9-36)a in an isolated rat heart", Pharmacol. Res., vol. 60, No. 5, pp. 411-417 (2009).

Petroff, et al., "Glucagon-like peptide-1 increases cAMP but fails to augment contraction in adult rat cardiac myocytes", Circ. Res., vol. 89, No. 5, pp. 445-452 (2001).

Poornima, et al., "Chronic Glucagon-Like Peptide-1 Infusion Sustains Left Ventricular Systolic Function and Prolongs Survival in the Spontaneously Hypertensive, Heart Failure—Prone Rat", Circ. Heart Fail., vol. 1, pp. 153-160 (2008).

Read, et al., "DPP-4 Inhibition by Sitagliptin Improves the Myocardial Response to Dobutamine Stress and Mitigates Stunning in a Pilot Study of Patients With Coronary Artery Disease," Circ. Cardiovasc. Imaging, vol. 3, pp. 195-201 (2010).

Sokos, et al., "Effect of glucagon-like peptide-1 (GLP-1) on glycemic control and left ventricular function in patients undergoing coronary artery bypass grafting," Am. J. Cardiol., vol. 100, No. 5, pp. 824-829 (2007).

Sokos, et al., "Glucagon-like peptide-1 infusion improves left ventricular ejection fraction and functional status in patients with chronic heart failure", J. Card. Fail. vol. 12, No. 9, pp. 694-699 (2006).

Sonne, et al., "Protective effects of GLP-1 analogues exendin-4 and GLP-1(9-36) amide against ischemia-reperfusion injury in rat heart", Regul. Pept. vol. 146, No. 1-3, pp. 243-249 (2008).

Taegtmeyer H., "Cardiac metabolism as a target for the treatment of heart failure", Circulation, vol. 110, No. 8, pp. 894-896 (2004).

Timmers, et al., "Exenatide reduces infarct size and improves cardiac function in a porcine model of ischemia and reperfusion injury", J. Am. Coll. Cardiol., vol. 53, No. 6, pp. 501-510 (2009).

Xiao, et al. "Bioogical Activities on Glucagon-Like Peptide-1 Analogues in Vitro and in Vivo." Biochemistry 40:2860-2869 (2001).

Xie, et al., "Effects and mechanism of glucagon-like peptide-1 on injury of rats cardiomyocytes induced by hypoxia-reoxygenation", Chin. Med. J. (Engl), vol. 121, No. 21, pp. 2134-2138 (2008).

Zhao, et al., "Direct effects of glucagon-like peptide-1 on myocardial contractility and glucose uptake in normal and postischemic isolated rat hearts", J. Pharmacol. Exp. Ther. vol. 317, No. 3, pp. 1106-1113 (2006).

* cited by examiner

Figure 1

SEQ ID NO.: 1

```
HGEGTFTSDVSSYLEGQAAKEFIAWLVKGRHGEGTFTSDVSSYLEGQAAKEFIAWLVKGR  60
DAHKSEVAHRFKDLGEENFKALVLIAFAQYLQQCPFEDHVKLVNEVTEFAKTCVADESAE 120
NCDKSLHTL FGDKLCTVATLRETYGEMADCCAKQEPERNECFLQHKDDNPNLPRLVRPE 180
VDVMCTAFHDNEETFLKKYLYEIARRHPYFYAPELLFFAKRYKAAFTECCQAADKAACLL 240
PKLDELRDEGKASSAKQRLKCASLQKFGERAFKAWAVARLSQRFPKAEFAEVSKLVTDLT 300
KVHTECCHGDLLECADDRADLAKYICENQDSISSKLKECCEKPLLEKSHCIAEVENDEMP 360
ADLPSLAADFVESKDVCKNYAEAKDVFLGMFLYEYARRHPDYSVVLLLRLAKTYETTLEK 420
CCAAADPHECYAKVFDEFKPLVEEPQNLIKQNCELFEQLGEYKFQNALLVRYTKKVPQVS 480
TPTLVEVSRNLGKVGSKCCKHPEAKRMPCAEDYLSVVLNQLCVLHEKTPVSDRVTKCCTE 540
SLVNRRPCFSALEVDETYVPKEFNAETFTFHADICTLSEKERQIKKQTALVELVKHKPKA 600
TKEQLKAVMDDFAAFVEKCCKADDKETCFAEEGKKLVAASQAALGL              674
```

Figure 2: Effects Of Albiglutide On HbA1c and ADA glycemic targets
A) Change from Baseline in HbA1c
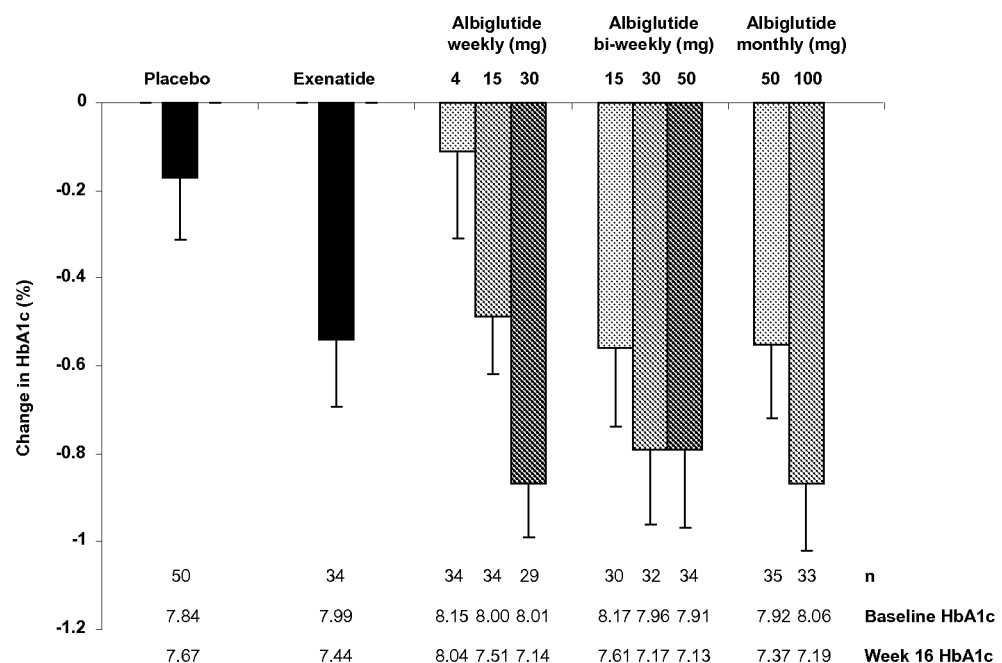
B) American Diabetes Association Responder Rates
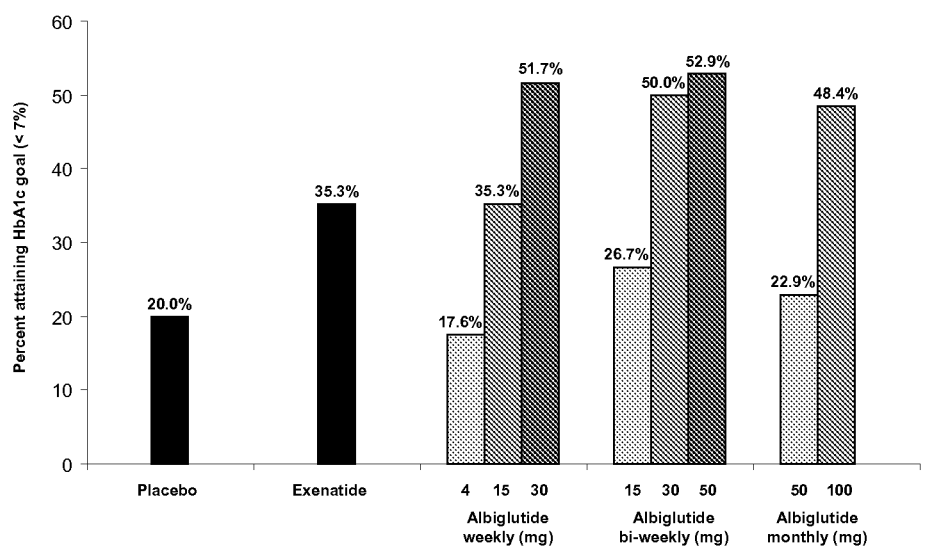

Figure 3: Effects Of Albiglutide On HbA1c and ADA glycemic targets
A. Weekly Dosing
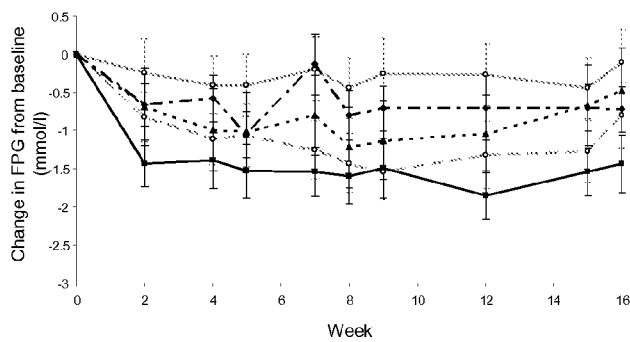
B. Biweekly Dosing
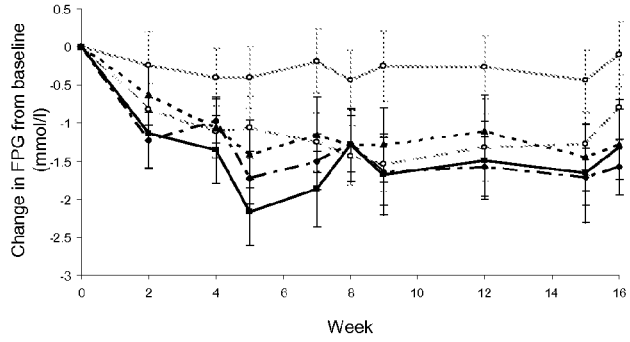
C. Monthly Dosing
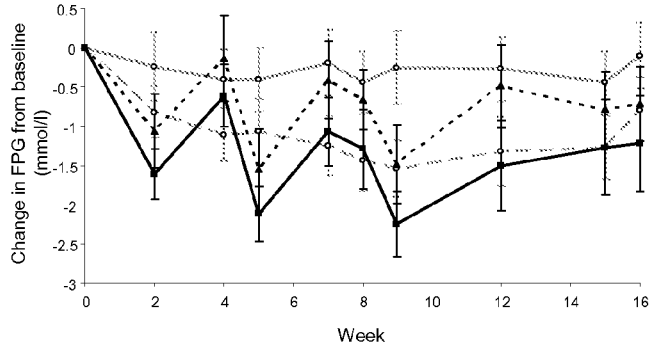

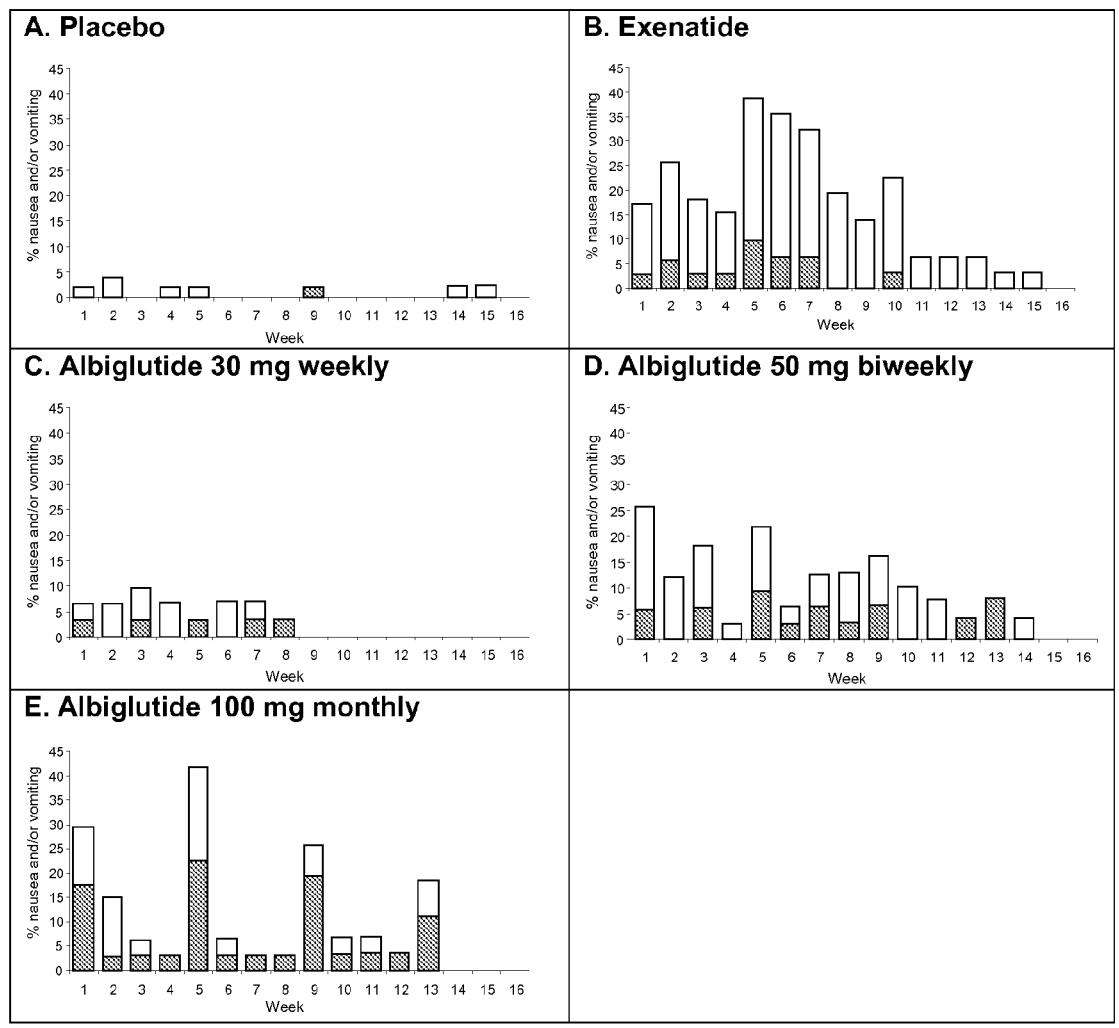
Figure 4: Time Course Of Nausea And Vomiting As Adverse Events

US 8,748,377 B2

PHARMACEUTICAL COMPOSITIONS

This application is a 371 of International Application No. PCT/US2009/067469, filed 10 Dec. 2009, which is incorporated herein by reference. This application also claims priority to and benefit of U.S. Provisional Application No. 61/121,229, filed 10 Dec. 2008, U.S. Provisional Application No. 61/150,909, filed 9 Feb. 2009, U.S. Provisional Application No. 61/163,995, filed 27 Mar. 2009 and U.S. Provisional Application No. 61/238,723, filed 1 Sep. 2009.

FIELD OF THE INVENTION

The present invention relates to pharmaceutical compositions and methods for administering long-lasting hypoglycemic agents and treatment regimens using compounds having GLP-1 activity and/or GLP-1 agonists.

BACKGROUND

Hypoglycemic agents may be used in the treatment of both type I and type II diabetes to lower glucose concentration in blood. Insulinotropic peptides have been implicated as possible therapeutic agents for the treatment of diabetes. Insulinotropic peptides include, but are not limited to, incretin hormones, for example, gastric inhibitory peptide (GIP) and glucagon like peptide-1 (GLP-1), as well as fragments, variants, and/or conjugates thereof. Insulinotropic peptides also include, for example, exendin 3 and exendin 4. GLP-1 is a 36 amino acid long incretin hormone secreted by the L-cells in the intestine in response to ingestion of food. GLP-1 has been shown to stimulate insulin secretion in a physiological and glucose-dependent manner, decrease glucagon secretion, inhibit gastric emptying, decrease appetite, and stimulate proliferation of β-cells. In non-clinical experiments GLP-1 promotes continued beta cell competence by stimulating transcription of genes important for glucose dependent insulin secretion and by promoting beta-cell neogenesis (Meier, et al. *Biodrugs*. 2003; 17 (2): 93-102).

In a healthy individual, GLP-1 plays an important role regulating post-prandial blood glucose levels by stimulating glucose-dependent insulin secretion by the pancreas resulting in increased glucose absorption in the periphery. GLP-1 also suppresses glucagon secretion, leading to reduced hepatic glucose output. In addition, GLP-1 delays gastric emptying and slows small bowel motility delaying food absorption.

In people with Type II Diabetes Mellitus (T2DM), the normal post-prandial rise in GLP-1 is absent or reduced (Vilsboll T, et al., *Diabetes*. 2001. 50; 609-613). Accordingly, one rationale for administering exogenous GLP-1, an incretin hormone, or an incretin mimetic, is to enhance, replace or supplement endogenous GLP-1 in order to increase meal-related insulin secretion, reduce glucagon secretion, and/or slow gastrointestinal motility. Native GLP-1 has a very short serum half-life (<5 minutes). Accordingly, it is not currently feasible to exogenously administer native GLP-1 as a therapeutic treatment for diabetes. Commercially available incretin mimetics such as Exenatide (Byetta®) improve glycemic control by reducing fasting and postprandial glucose concentrations when administered subcutaneously (5 μg or 10 μg BID) to patients with T2DM.

Thus, there is an unmet need for methods of administering hypoglycemic agents wherein the hypoglycaemic agent is administered at an effective weekly or monthly dose.

BRIEF DESCRIPTION OF THE DRAWINGS

FIG. 1. SEQ ID NO.:1.
FIG. 2: Effects of Albiglutide, Exenatide and Placebo on HbA1c and ADA glycemic targets.
FIG. 3: Effects of Albiglutide, Exenatide and Placebo on HbA1c and ADA glycemic targets.
FIG. 4: Time Course of Nausea and Vomiting as Adverse Events among Patients Receiving Albiglutide, Exenatide and Placebo.

SUMMARY OF THE INVENTION

The present invention provides pharmaceutical compositions comprising at least one polypeptide having GLP-1 activity wherein an effective dose of said pharmaceutical composition comprises 15 mg, 30 mg, 50 mg or 100 mg of said polypeptide having GLP-1 activity.

The present invention further provides methods of administering at least one polypeptide having GLP-1 activity to a human comprising administering a pharmaceutical composition of the present invention to a human.

DEFINITIONS

"GLP-1 agonist composition" as used herein means any composition capable of stimulating the secretion of insulin, or otherwise raising the level of insulin, including, but not limited to an incretin hormone and an incretin mimetic.

"Incretin hormone" as used herein means any hormone that potentiates insulin secretion or otherwise raises the level of insulin in a mammal. One example of an incretin hormone is GLP-1. GLP-1 is an incretin secreted by intestinal L cells in response to ingestion of food. In a healthy individual, GLP-1 plays an important role regulating post-prandial blood glucose levels by stimulating glucose-dependent insulin secretion by the pancreas resulting in increased glucose absorption in the periphery. GLP-1 also suppresses glucagon secretion, leading to reduced hepatic glucose output. In addition, GLP-1 delays gastric emptying time and slows small bowel motility delaying food absorption. GLP-1 promotes continued beta cell competence by stimulating transcription of genes involved in glucose dependent insulin secretion and by promoting beta-cell neogenesis (Meier, et al. *Biodrugs* 2003; 17 (2): 93-102).

"GLP-1 activity" as used herein means one or more of the activities of naturally occurring human GLP-1, including but not limited to, reducing blood and/or plasma glucose, stimulating glucose-dependent insulin secretion or otherwise raising the level or insulin, suppressing glucagon secretion, reducing fructosamine, increases glucose delivery and metabolism to the brain, delaying gastric emptying, and promoting beta cell competence, and/or neogenesis. Any of these activities and other activity associated with GLP-1 activity may be caused directly or indirectly by a composition having GLP-1 activity or a GLP-1 agonist. By way of example, a composition having GLP-1 activity may directly or indirectly stimulate glucose-dependent while the stimulation of insulin production may indirectly reduce plasma glucose levels in a mammal.

An "incretin mimetic" as used herein is a compound capable of potentiating insulin secretion or otherwise raise the level or insulin. An incretin mimetic may be capable of stimulating insulin secretion, increasing beta cell neogenesis, inhibiting beta cell apoptosis, inhibiting glucagon secretion, delaying gastric emptying and inducing satiety in a mammal. An incretin mimetic may include, but is not limited to, any polypeptide which has GLP-1 activity, including but not limited to, exendin 3 and exendin 4, including any fragments and/or variants and/or conjugates thereof.

"Hypoglycemic agent" as used herein means any compound or composition comprising a compound capable of reducing blood glucose. A hypoglycemic agent may include, but is not limited to, any GLP-1 agonist including incretin hormones or incretin mimetics, GLP-1 and/or fragment, variant and/or conjugate thereof. Other hypoglycemic agents include, but are not limited to, drugs that increase insulin secretion (e.g., sulfonylureas (SU) and meglitinides), inhibit GLP-1 break down (e.g., DPP-IV inhibitors), increase glucose utilization (e.g., glitazones, thiazolidinediones (TZDs) and/or pPAR agonists), reduce hepatic glucose production (e.g., metformin), and delay glucose absorption (e.g., α-glucosidase inhibitors). Examples of sulfonylureas include but are not limited to acetohexamide, chlorpropamide, tolazamide, glipizide, gliclazide, glibenclamide (glyburide), gliquidone, and glimepiride. Examples of glitazones include, but are not limited to, rosiglitazone and pioglitazone.

"Polynucleotide(s)" generally refers to any polyribonucleotide or polydeoxyribonucleotide that may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide(s)" also includes DNAs or RNAs as described above that comprise one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques that are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W.H. Freeman and Company, New York, 1993 and Wold, F., Posttranslational Protein Modifications: Perspectives and Prospects, pgs. 1-12 in POSTTRANSLATIONAL COVALENT MODIFICATION OF PROTEINS, B. C. Johnson, Ed., Academic Press, New York, 1983; Seifter, et al., "Analysis for protein modifications and nonprotein cofactors", *Meth. Enzymol.* (1990) 182:626-646 and Rattan, et al., "Protein Synthesis: Posttranslational Modifications and Aging", *Ann NY Acad Sci* (1992) 663:48-62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis. Variants may also include, but are not limited to, polypeptides or fragments thereof having chemical modification of one or more of its amino acid side groups. A chemical modification includes, but is not limited to, adding chemical moieties, creating new bonds, and removing chemical moieties. Modifications at amino acid side groups include, without limitation, acylation of lysine-ε-amino groups, N-alkylation of arginine, histidine, or lysine, alkylation of glutamic or aspartic carboxylic acid groups, and deamidation of glutamine or asparagine. Modifications of the terminal amino group include, without limitation, the des-amino, N-lower alkyl, N-di-lower alkyl, and N-acyl modifications. Modifications of the terminal carboxy group include, without limitation, the amide, lower alkyl amide, dialkyl amide, and lower alkyl ester modifications. Furthermore, one or more side groups, or terminal groups, may be protected by protective groups known to the ordinarily-skilled protein chemist.

As used herein "fragment," when used in reference to a polypeptide, is a polypeptide having an amino acid sequence that is the same as part but not all of the amino acid sequence of the entire naturally occurring polypeptide. Fragments may be "free-standing" or comprised within a larger polypeptide of which they form a part or region as a single continuous region in a single larger polypeptide. By way of example, a fragment of naturally occurring GLP-1 would include amino acids 7 to 36 of naturally occurring amino acids 1 to 36. Furthermore, fragments of a polypeptide may also be variants of the naturally occurring partial sequence. For instance, a fragment of GLP-1 comprising amino acids 7-30 of naturally occurring GLP-1 may also be a variant having amino acid substitutions within its partial sequence.

As used herein "conjugate" or "conjugated" refers to two molecules that are bound to each other. For example, a first polypeptide may be covalently or non-covalently bound to a second polypeptide. The first polypeptide may be covalently bound by a chemical linker or may be genetically fused to the second polypeptide, wherein the first and second polypeptide share a common polypeptide backbone.

As used herein "tandemly oriented" refers to two or more polypeptides that are adjacent to one another as part of the same molecule. They may be linked either covalently or non-covalently. Two or more tandemly oriented polypeptides may form part of the same polypeptide backbone. Tandemly oriented polypeptides may have direct or inverted orientation and/or may be separated by other amino acid sequences.

As used herein, "reduce" or "reducing" blood or plasma glucose refers to a decrease in the amount of blood glucose observed in the blood of a patient after administration a hypoglycemic agent. Reductions in blood or plasma glucose can be measured and assessed per individual or as a mean change for a group of subjects. Additionally, mean reductions in blood or plasma glucose can be measured and assessed for a group of treated subjects as a mean change from baseline and/or as a mean change compared with the mean change in blood or plasma glucose among subjects administered placebo.

As used herein "enhancing GLP-1 activity" refers to an increase in any and all of the activities associated with naturally occurring GLP-1. By way of example, enhancing GLP-1 activity can be measured after administration of at least one polypeptide having GLP-1 activity to a subject and compared with GLP-1 activity in the same subject prior to the administration of the polypeptide having GLP-1 activity or in comparison to a second subject who is administered placebo.

As used herein "diseases associated with elevated blood glucose" include, but are not limited to, type I and type II diabetes, glucose intolerance, and hyperglycemia.

As used herein "co-administration" or "co-administering" refers to administration of two or more compounds or two or more doses of the same compound to the same patient. Co-administration of such compounds may be simultaneous or at about the same time (e.g., within the same hour) or it may be within several hours or days of one another. For example, a first compound may be administered once weekly while a second compound is co-administered daily.

As used herein "maximum plasma concentration" or "Cmax" means the highest observed concentration of a substance (for example, a polypeptide having GLP-1 activity or a GLP-1 agonist) in mammalian plasma after administration of the substance to the mammal.

As used herein "Area Under the Curve" or "AUC" is the area under the curve in a plot of the concentration of a substance in plasma against time. AUC can be a measure of the integral of the instantaneous concentrations during a time interval and has the units mass×time/volume, which can also be expressed as molar concentration×time such as nM×day. AUC is typically calculated by the trapezoidal method (e.g., linear, linear-log). AUC is usually given for the time interval zero to infinity, and other time intervals are indicated (for example AUC (t1,t2) where t1 and t2 are the starting and finishing times for the interval). Thus, as used herein "$AUC_{0-24h}$" refers to an AUC over a 24-hour period, and "$AUC_{0-4h}$" refers to an AUC over a 4-hour period.

As used herein "weighted mean AUC" is the AUC divided by the time interval over which the time AUC is calculated. For instance, weighted mean $AUC_{0-24h}$ would represent the $AUC_{0-24h}$ divided by 24 hours.

As used herein "confidence interval" or "CI" is an interval in which a measurement or trial falls corresponding to a given probability p where p refers to a 90% or 95% CI and are calculated around either an arithmetic mean, a geometric mean, or a least squares mean. As used herein, a geometric mean is the mean of the natural log-transformed values back-transformed through exponentiation, and the least squares mean may or may not be a geometric mean as well but is derived from the analysis of variance (ANOVA) model using fixed effects.

As used herein the "coefficient of variation (CV)" is a measure of dispersion and it is defined as the ratio of the standard deviation to the mean. It is reported as a percentage (%) by multiplying the above calculation by 100 (% CV).

As used herein "Tmax" refers to the observed time for reaching the maximum concentration of a substance in plasma of a mammal after administration of that substance to the mammal.

As used herein "serum or plasma half life" refers to the time required for half the quantity of a substance administered to a mammal to be metabolized or eliminated from the serum or plasma of the mammal by normal biological processes.

As used herein "dose" refers to any amount of therapeutic compound which may be administered to a mammal, including a human. An effective dose is a dose of a compound that is in an amount sufficient to induce at least one of the intended effects of the therapeutic compound. For instance, an effective dose of a GLP-1 agonist would induce at least one type of GLP-1 activity in a human when administered to a human, such as, but not limited to increasing insulin production in said human. As is understood in the art, an effective dose of a therapeutic compound can be measured by a surrogate endpoint. Thus, by way of another example, an effective dose of a GLP-1 agonist can be measured by its ability to lower serum glucose in a human.

As used herein "cardiovascular disorder" include, but is not limited to, cardiovascular abnormalities, such as arterio-arterial fistula, arteriovenous fistula, cerebral arteriovenous malformations, congenital heart defects, pulmonary atresia, and Scimitar Syndrome. Congenital heart defects include, but are not limited to, aortic coarctation, cor triatriatum, coronary vessel anomalies, crisscross heart, dextrocardia, patent ductus arteriosus, Ebstein's anomaly, Eisenmenger complex, hypoplastic left heart syndrome, levocardia, tetralogy of fallot, transposition of great vessels, double outlet right ventricle, tricuspid atresia, persistent truncus arteriosus, and heart septal defects, such as aortopulmonary septal defect, endocardial cushion defects, Lutembacher's Syndrome, trilogy of Fallot, ventricular heart septal defects.

Cardiovascular disorders also include, but are not limited to, chronic cardiac failure, heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, diabetic cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Arrhythmias include, but are not limited to, sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve diseases include, but are not limited to, aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include, but are not limited to, alcoholic cardiomyopathy, diabetic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include, but are not limited to, coronary disease, such as angina pectoris, coronary aneurysm, coronary arteriosclerosis, coronary thrombosis, coronary vasospasm, myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular disorders, diabetic angiopathies, diabetic retinopathy, embolisms, thrombosis, erythromelaigia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

DETAILED DESCRIPTION OF THE INVENTION

The present invention provides pharmaceutical compositions comprising at least one polypeptide having GLP-1 activity wherein an effective dose of said pharmaceutical composition comprises 15 mg, 30 mg, 50 mg, or 100 mg of said polypeptide having GLP-1 activity. In some aspects, the polypeptide having GLP-1 activity comprises at least one GLP-1 agonist. GLP-1 agonists can be selected from the group of: incretin hormone and/or fragment, variant and/or conjugate thereof and incretin mimetic and/or fragment, variant and/or conjugate thereof. Included among incretin hormones are human GLP-1 and/or fragments, variants and/or conjugates thereof.

An embodiment of the invention comprises a polypeptide that may be, but is not limited to, GLP-1 or a fragment, variant, and/or conjugate thereof. GLP-1 fragments and/or variants and/or conjugates of the present invention typically have at least one GLP-1 activity. A GLP-1 or a fragment, variant, and/or conjugate thereof may comprise human serum albumin. Human serum albumin may be conjugated to the GLP-1 or fragment and/or variant thereof. Human serum albumin may be conjugated to an incretin hormone (such as GLP-1) and/or incretin mimetic (such as exendin 3 and exendin 4) and/or fragments and/or variants thereof through a chemical linker prior to injection or may be chemically linked to naturally occurring human serum albumin in vivo (see for instance, U.S. Pat. No. 6,593,295 and U.S. Pat. No. 6,329,336, herein incorporated by reference in their entirety). Alternatively, human serum albumin may be genetically fused to a GLP-1 and/or fragment and/or variant thereof or other GLP-1 agonist such as exendin-3 or exendin-4 and/or fragments and/or variants thereof. Examples of GLP-1 and fragments and/or variants thereof fused with human serum albumin are provided in the following: WO 2003/060071, WO 2003/59934, WO 2005/003296, WO 2005/077042 and U.S. Pat. No. 7,141,547 (herein incorporated by reference in their entirety).

Polypeptides having GLP-1 activity may comprise at least one fragment and/or variant of human GLP-1. The two naturally occurring fragments of human GLP-1 are represented in SEQ ID NO: 2.

```
                                        (SEQ ID NO.: 2)
 7   8   9  10  11  12  13  14  15  16  17
His-Ala-Glu-Gly-Thr-Phe-Thr-Ser-Asp-Val-Ser- 18  19  20  21  22  23  24  25  26  27  28
Ser-Tyr-Leu-Glu-Gly-Gln-Ala-Ala-Lys-Glu-Phe- 29  30  31  32  33  34  35  36  37
Ile-Ala-Trp-Leu-Val-Lys-Gly-Arg-Xaa
``` wherein: Xaa at position 37 is Gly (hereinafter designated as "GLP-1(7-37)"), or —NH$_2$ (hereinafter designated as "GLP-1(7-36)"). GLP-1 fragments may include, but are not limited to, molecules of GLP-1 comprising, or alternatively consisting of, amino acids 7 to 36 of human GLP-1 (GLP-1(7-36)). Variants of GLP-1 or fragments thereof may include, but are not limited to, one, two, three, four, five or more amino acid substitutions in wild type GLP-1 or in the naturally occurring fragments of GLP-1 shown in SEQ ID NO.: 2. Variants GLP-1 or fragments of GLP-1 may include, but are not limited to, substitutions of an alanine residue analogous to alanine 8 of wild type GLP-1, such alanine being mutated to a glycine (hereinafter designated as "A8G") (See for example, the mutants disclosed in U.S. Pat. No. 5,545,618, herein incorporated by reference in its entirety).

In some aspects, at least one fragment and variant of GLP-1 comprises GLP-1(7-36(A8G)) and is genetically fused to human serum albumin. In a further embodiment, polypeptides of the invention comprise one, two, three, four, five, or more tandemly oriented molecules of GLP-1 and/or fragments and/or variants thereof fused to the N- or C-terminus of human serum albumin or variant thereof. Other embodiments have such A8G polypeptides fused to the N- or C-terminus of albumin or variant thereof. An example of two tandemly oriented GLP-1(7-36) (A8G) fragments and/or variants fused to the N-terminus of human serum albumin comprises SEQ ID NO:1, which is presented in FIG. 1. In another aspect, at least one fragment and variant of GLP-1 comprises at least two GLP-1(7-36(A8G)) tandemly and genetically fused to the human serum albumin. At least two GLP-1(7-36(A8G)) may be genetically fused at the N-terminus of the human serum albumin. At least one polypeptide having GLP-1 activity may comprise SEQ ID No.: 1.

Variants of GLP-1(7-37) may be denoted for example as $Glu^{22}$-GLP-1(7-37)OH which designates a GLP-1 variant in which the glycine normally found at position 22 of GLP-1(7-37)OH has been replaced with glutamic acid; $Val^8$-$Glu^{22}$-GLP-1(7-37)OH designates a GLP-1 compound in which alanine normally found at position 8 and glycine normally found at position 22 of GLP-1(7-37)OH have been replaced with valine and glutamic acid, respectively. Examples of variants of GLP-1 include, but are not limited to, of arginine, histidine, or lysine, alkylation of glutamic or aspartic carboxylic acid groups, and deamidation of glutamine or asparagine. Modifications of the terminal amino group include, without limitation, the des-amino, N-lower alkyl, N-di-lower alkyl, and N-acyl modifications. Modifications of the terminal carboxy group include, without limitation, the amide, lower alkyl amide, dialkyl amide, and lower alkyl ester modifications. Furthermore, one or more side groups, or terminal groups, may be protected by protective groups known to the ordinarily-skilled protein chemist.

GLP-1 fragments or variants may also include polypeptides in which one or more amino acids have been added to the N-terminus and/or C-terminus of GLP-1(7-37)OH of said fragment or variant. The amino acids in GLP-1 in which amino acids have been added to the N-terminus or C-terminus are denoted by the same number as the corresponding amino acid in GLP-1(7-37)OH. For example, the N-terminus amino acid of a GLP-1 compound obtained by adding two amino acids to the N-terminus of GLP-1(7-37)OH is at position 5; and the C-terminus amino acid of a GLP-1 compound obtained by adding one amino acid to the C-terminus of GLP-1(7-37)OH is at position 38. Thus, position 12 is occupied by phenylalanine and position 22 is occupied by glycine in both of these GLP-1 compounds, as in GLP-1(7-37)OH. Amino acids 1-6 of a GLP-1 with amino acids added to the N-terminus may be the same as or a conservative substitution of the amino acid at the corresponding position of GLP-1(1-37)OH. Amino acids 38-45 of a GLP-1 with amino acids added to the C-terminus may be the same as or a conservative substitution of the amino acid at the corresponding position of glucagon or exendin-4.

| | | |
|---|---|---|
| $Val^8$-GLP-1(7-37)OH | $Gly^8$-GLP-1(7-37)OH | $Glu^{22}$-GLP-1(7-37)O-H |
| $Asp^{22}$-GLP-1(7-37)OH | $Arg^{22}$-GLP-1(7-37)OH | $Lys^{22}$-GLP-1(7-37)OH |
| $Cys^{22}$-GLP-1(7-37)OH | $Val^8$-$Glu^{22}$-GLP-1(7-37)OH | $Val^8$-$Asp^{22}$-GLP-1(7-37)OH |
| $Val^8$-$Arg^{22}$-GLP-1(7-37)OH | $Val^8$-$Lys^{22}$-GLP-1(7-37)OH | $Val^8$-$Cys^{22}$-GLP-1(7-37)OH |
| $Gly^8$-$Glu^{22}$-GLP-1(7-37)OH | $Gly^8$-$Asp^{22}$-GLP-1(7-37)OH | $Gly^8$-$Arg^{22}$-GLP-1(7-37)OH |
| $Gly^8$-$Lys^{22}$-GLP-1(7-37)OH | $Gly^8$-$Cys^{22}$-GLP-1(7-37)OH | $Glu^{22}$-GLP-1(7-36)OH |
| $Asp^{22}$-GLP-1(7-36)OH | $Arg^{22}$-GLP-1(7-36)OH | $Lys^{22}$-GLP-1(7-36)OH |
| $Cys^{22}$-GLP-1(7-36)OH | $Val^8$-$Glu^{22}$-GLP-1(7-36)OH | $Val^8$-$Asp^{22}$-GLP-1(7-36)OH |
| $Val^8$-$Arg^{22}$-GLP-1(7-36)OH | $Val^8$-$Lys^{22}$-GLP-1(7-36)OH | $Val^8$-$Cys^{22}$-GLP-1(7-36)OH |
| $Gly^8$-$Glu^{22}$-GLP-1(7-36)OH | $Gly^8$-$Asp^{22}$-GLP-1(7-36)OH | $Gly^8$-$Arg^{22}$-GLP-1(7-36)OH |
| $Gly^8$-$Lys^{22}$-GLP-1(7-36)OH | $Gly^8$-$Cys^{22}$-GLP-1(7-36)OH | $Lys^{23}$-GLP-1(7-37)OH |
| $Val^8$-$Lys^{23}$-GLP-1(7-37)OH | $Gly^8$-$Lys^{23}$-GLP-1(7-37)OH | $His^{24}$-GLP-1(7-37)OH |
| $Val^8$-$His^{24}$-GLP-1(7-37)OH | $Gly^8$-$His^{24}$-GLP-1(7-37)OH | $Lys^{24}$-GLP-1(7-37)OH |
| $Val^8$-$Lys^{24}$-GLP-1(7-37)OH | $Gly^8$-$Lys^{23}$-GLP-1(7-37)OH | $Glu^{30}$-GLP-1(7-37)OH |
| $Val^8$-$Glu^{30}$-GLP-1(7-37)OH | $Gly^8$-$Glu^{30}$-GLP-1(7-37)OH | $Asp^{30}$-GLP-1(7-37)OH |
| $Val^8$-$Asp^{30}$-GLP-1(7-37)OH | $Gly^8$-$Asp^{30}$-GLP-1(7-37)OH | $Gln^{30}$-GLP-1(7-37)OH |
| $Val^8$-$Gln^{30}$-GLP-1(7-37)OH | $Gly^8$-$Gln^{30}$-GLP-1(7-37)OH | $Tyr^{30}$-GLP-1(7-37)OH |
| $Val^8$-$Tyr^{30}$-GLP-1(7-37)OH | $Gly^8$-$Tyr^{30}$-GLP-1(7-37)OH | $Ser^{30}$-GLP-1(7-37)OH |
| $Val^8$-$Ser^{30}$-GLP-1(7-37)OH | $Gly^8$-$Ser^{30}$-GLP-1(7-37)OH | $His^{30}$-GLP-1(7-37)OH |
| $Val^8$-$His^{30}$-GLP-1(7-37)OH | $Gly^8$-$His^{30}$-GLP-1(7-37)OH | $Glu^{34}$-GLP-1(7-37)OH |
| $Val^8$-$Glu^{34}$-GLP-1(7-37)OH | $Gly^8$-$Glu^{34}$-GLP-1(7-37)OH | $Ala^{34}$-GLP-1(7-37)OH |
| $Val^8$-$Ala^{34}$-GLP-1(7-37)OH | $Gly^8$-$Ala^{34}$-GLP-1(7-37)OH | $Gly^{34}$-GLP-1(7-37)OH |
| $Val^8$-$Gly^{34}$-GLP-1(7-37)OH | $Gly^8$-$Gly^{34}$-GLP-1(7-37)OH | $Ala^{35}$-GLP-1(7-37)OH |
| $Val^8$-$Ala^{35}$-GLP-1(7-37)OH | $Gly^8$-$Ala^{35}$-GLP-1(7-37)OH | $Lys^{35}$-GLP-1(7-37)OH |
| $Val^8$-$Lys^{35}$-GLP-1(7-37)OH | $Gly^8$-$Lys^{35}$-GLP-1(7-37)OH | $His^{35}$-GLP-1(7-37)OH |
| $Val^8$-$His^{35}$-GLP-1(7-37)OH | $Gly^8$-$His^{35}$-GLP-1(7-37)OH | $Pro^{35}$-GLP-1(7-37)OH |
| $Val^8$-$Pro^{35}$-GLP-1(7-37)OH | $Gly^8$-$Pro^{35}$-GLP-1(7-37)OH | $Glu^{35}$-GLP-1(7-37)OH |
| $Gly^8$-$Glu^{35}$-GLP-1(7-37)OH | $Val^8$-$Ala^{27}$-GLP-1(7-37)OH | $Val^8$-$His^{37}$-GLP-1(7-37)OH |
| $Val^8$-$Glu^{22}$-$Lys^{23}$-GLP-1(7-37)OH | $Val^8$-$Glu^{22}$-$Glu^{23}$-GLP-1(7-37)OH | $Val^8$-$Glu^{22}$-$Ala^{27}$-GLP-1(7-37)OH |
| $Val^8$-$Gly^{34}$-$Lys^{35}$-GLP-1(7-37)OH | $Val^8$-$His^{37}$-GLP-1-(7-37)OH | $Gly^8$-$His^{37}$-GLP-1(7-37)OH |
| $Val^8$-$Glu^{22}$-$Ala^{27}$-GLP-1(7-37)OH | $Gly^8$-$Glu^{22}$-$Ala^{27}$-GLP-1(7-37)OH | $Val^8$-$Lys^{22}$-$Glu^{23}$-GLP-1(7-37)OH |
| $Gly^8$-$Lys^{22}$-$Glu^{23}$-GLP-1(7-37)OH. | $Val^8$-$Glu^{35}$-GLP-1(7-37)OH | |

Variants of GLP-1 may also include, but are not limited to, GLP-1 or GLP-1 fragments having chemical modification of one or more of its amino acid side groups. A chemical modification includes, but is not limited to, adding chemical moieties, creating new bonds, and removing chemical moieties. Modifications at amino acid side groups include, without limitation, acylation of lysine-ε-amino groups, N-alkylation In another embodiment, the pharmaceutical composition of the present invention can administered to a human once daily, once every other day, once every seven days, once every fourteen days, once every four weeks, and/or once every month. In another aspect, the pharmaceutical compositions comprises at least 30 mg/mL of SEQ ID NO:1. In another aspect, the pharmaceutical composition consists of 30 mg/mL of SEQ ID NO:1, sodium phosphate, trehalose, mannitol, TWEEN 80 and water and is maintained at pH 7.2. In another aspect, the pharmaceutical composition consists of 50 mg/mL of SEQ ID NO:1, sodium phosphate, trehalose, mannitol, TWEEN 80 and water and is maintained at pH 7.2.

In another aspect, methods are provided for administering at least one polypeptide having GLP-1 activity to a human comprising administering a pharmaceutical composition of the invention to a human. Pharmaceutical composition can be administered subcutaneously. Pharmaceutical composition can be administered as a subcutaneous injection selected from the group of: at least one 0.32 mL injection, at least one 0.65 mL injection, and at least one 1.0 mL injection. In some aspects, the pharmaceutical composition is co-administered in two injections, which may be the same dose or may be different doses of the same pharmaceutical composition. The pharmaceutical compositions of the present invention may be administered at the same or different injection sites. Subcutaneous injections of the invention may be administered as single injections, meaning the entire dose is administered as a single shot, wherein the entire volume of the shot is administered all at once. A single shot differs from a continuous administration which may be administered over several minutes and/or hours and/or days. Single injections may be administered multiple times, meaning as a single shot once daily, weekly, every two weeks, monthly and/or more.

In another aspect, the pharmaceutical composition reduces HbA1c in said human and/or serum glucose in said human. The serum half life of said at least one polypeptide having GLP-1 activity, for example SEQ ID NO:1, is about 5 days. In another aspect, the human has a disease associated with elevated glucose levels which may include hyperglycemia, diabetes, type II diabetes. In yet another aspect, the pharmaceutical compositions of the present invention cause weight loss in a human when administered to a human.

In another embodiment, pharmaceutical compositions of the present invention are administered as monotherapy. In yet another embodiment, the pharmaceutical compositions is co-administered with at least one second hypoglycaemic agent. A second hypoglycaemic agent may be selected from: a GLP-1 agonist, incretin hormone, incretin mimetic, agent to increase insulin secretion, sulfonylurea, meglitinide, acetohexamide, chlorpropamide, tolazamide, glipizide, gliclazide, glibenclamide (glyburide), gliquidone, glimepiride, agent to inhibit GLP-1 break down, DPP-IV inhibitor, agent to increase glucose utilization, glitazones, thiazolidinediones, rosiglitazone, pioglitazone, pPAR agonists, agent to reduce hepatic glucose production, metformin, agent to delay glucose absorption, α-glucosidase inhibitor, insulin glargine and/or insulin. In some aspects, the second hypoglycaemic agent is metformin. In some aspects of the present invention, the polypeptide having GLP-1 activity is administered to said human at an initial dose of 30 mg and subsequently titrated up to 50 mg. The skilled artisan will understand that pharmaceutical compositions can be administered to humans who are no longer responding to their current therapy. That is, a subject may have a wash-out period from current therapy while concurrently or sequentially starting therapy with a pharmaceutical composition of the present invention.

As is understood in the art, various methods may be employed to collect, measure and assess pharmacokinetic data such as active compound concentration in blood, plasma and/or other tissue. As is also understood in the art, various methods may be employed to collect, measure and assess various pharmacodynamic data such as, but not limited to, glucose, insulin, C peptide, glucagon and other biomarker levels in blood and/or plasma and/or other tissue.

A skilled artisan will understand the various methods for measuring and calculating the pharmacokinetic (for example, but not limited to, Cmax, AUC, Tmax, serum half-life) and pharmacodynamic (for example, but not limited to, serum and/or plasma blood glucose levels and/or HbA1c levels) parameters described herein. Furthermore, the skilled artisan will understand the various methods for making statistical comparisons (for example, but not limited to, comparisons of change from baseline to post-treatment and/or comparisons among treatment groups) and/or analysis of the pharmacokinetic and pharmacodynamic parameters described herein. Furthermore, the skilled artisan will understand and be able to employ various other methods for collecting and analyzing pharmacokinetic, pharmacodynamic and other clinical data.

Furthermore, the present invention includes pharmaceutical compositions as well as methods of making the pharmaceutical compositions and methods of using the pharmaceutical compositions of the present invention. The pharmaceutical compositions of the present invention can be used in treatment or prophylactically to treat, prevent and/or prevent the worsening of any symptom of any disease or condition associated with elevated glucose, obesity, cardiovascular disorders, including but not limited to myocardial infarction, and chronic heart failure, and/or memory loss.

EXAMPLES

The following examples illustrate various non-limiting aspects of this invention. For the following examples, unless noted otherwise, SEQ ID NO.:1 also referred to herein as Albiglutide (ALB) was formulated as 50 mg/mL from a lyophilized form comprising 2.8% mannitol, 4.2% trehalose dihydrate, 0.01% polysorbate 80, 10 to 20 mM phosphate buffer at pH 7.2. Compositions comprising SEQ ID NO.:1 were diluted with water for injection as necessary for respective dosing.

Example 1

The Potential of Albiglutide, a Long-Acting GLP-1 Mimetic, in Type 2 Diabetes: A Randomized Controlled Trial Exploring Weekly, Biweekly and Monthly Dosing This study was designed to evaluate the efficacy, safety and tolerability of incremental doses of albiglutide (ALB), a long-acting GLP-1-receptor agonist, administered with 3 timing schedules in type 2 diabetic patients inadequately controlled with diet and exercise or metformin monotherapy. Albiglutide (ALB) consists of a DPP-4-resistant GLP-1 dimer fused to human albumin. With a half-life of ~5 days, ALB has the potential for weekly or less-frequent dosing. In this randomized multicenter, double-blind, parallel-group study in 356 type 2 diabetic subjects with similar mean baseline characteristics (age 53.4 years, diabetes duration 5 years, BMI 32 kg/m$^2$, A1C 8.0%), patients received subcutaneous placebo, albiglutide [weekly (4, 15 or 30 mg), every-other week (biweekly; 15, 30 or 50 mg) or monthly (50 or 100 mg)], or exenatide as an open-label active reference (twice-daily per labeling in metformin patients only) over 16 weeks, followed by an 11-week washout period. Main outcome measure was change from baseline A1C, week 16 vs placebo.

Outcomes studies show that early intervention to improve glycemic control reduces microvascular complications in type 2 diabetes (UK Prospective Diabetes Study (UKPDS) (UKPDS 33). *Lancet* 352:837-853, 1998; Gerstein, et al. *N Engl J Med* 358:2545-2559, 2008; Patel, et al. *N Engl J Med*

358:2560-2572, 2008; and Abrair, et al. *Diabetes Obes Metab* 2008; DOI: 10.1111/j.1463-1326.2008.00933.x) and may provide long-term macrovascular benefit (Holma, et al. *N Engl J Med* 359:1577-1589, 2008). Despite numerous available therapies, over half of patients with type 2 diabetes are unable to achieve the American Diabetes Association (ADA) target A1C level (<7%) (Saydah, et al. *JAMA* 291:335-342, 2004; Saaddine, et al. *Ann Intern Med* 144(7):465-474, 2006; Ong K L, et al. *Ann Epidemiol* 18:222-229, 2008). Moreover, weight gain and treatment-induced hypoglycemic episodes (Carver. *Diabetes Educ* 32:910-917, 2006 and Kahn, et al. *N Engl J Med* 355:2427-2443, 2006) are major barriers to achieving glycemic control (Bray GM. Exenatide. *Am J Health Syst Pharm* 63:411-418, 2006). Antidiabetic therapies, based on glucagon-like peptide-1 (GLP-1), retain the ability of native GLP-1 to stimulate glucose-dependent insulin secretion and suppress inappropriately elevated post-meal glucagon secretion (Drucker, et al. *Proc Natl Acad Sci USA* 84:3434-3438, 1987; Kreymann, et al. *Lancet* 2:1300-1304, 1987). Native GLP-1 also slows gastric emptying and reduces food intake, leading to modest weight loss in patients with T2DM. (Hols, et al. Trends Moled Med 14(4):161-168, 2008). However, native GLP-1 is rapidly inactivated (half-life: 1-2 minutes) by dipeptidyl peptidase-4 (DPP-4), limiting its therapeutic potential (Deacon, et al. *Am J Physiol* 271(3 Pt 1):E458-E464, 1996). Exenatide (half-life: 2.4 hours) improves glycemic control in combination with metformin, sulfonylurea or a thiazolidinedione. (BYETTA® exenatide injection. Prescribing information; DeFronzo, et al. *Diabetes Care* 28:1092-1100, 2005; Kendall, et al. *Diabetes Care* 28:1083-1091, 2005; Zinman, et al. *Ann Intern Med* 146:477-485, 2007; Buse, et al. *Diabetes Care* 27:2628-2635, 2004). Despite modest weight loss and improved glycemic control, gastrointestinal (GI) intolerability and the need for twice-daily injections often leads to discontinuation (Fineman, et al. *Diabetes Metab Res Rev* 20:411-417, 2004).

Albiglutide is a GLP-1 receptor agonist developed by fusion of two DPP-4-resistant human GLP-1 analogs to human albumin (Matthews, et al. *J Clin Endocrinol Metab.* 2008; DOI: 10.1210/jc.2008-1518). Its extended half-life (~5 days) may allow weekly or less-frequent dosing. This study was designed to explore a wide range of doses (4-100 mg) and schedules (weekly-to-monthly) to assess glycemic control and adverse event profiles. Exenatide was included as an open-label reference to provide clinical perspective for a GLP-1 receptor agonist.

Research Design and Methods
Protocol

This phase 2 trial was a prospective, randomized, double-blind, placebo-controlled, parallel group study conducted between April 2007 and May 2008 in 118 sites in the United States (n=106), Mexico (n=9), Chile (n=2), and the Dominican Republic (n=1). Men and women of non-childbearing potential from 18-75 years of age were eligible for inclusion if diagnosed with type 2 diabetes ≥3 months before screening. Subjects were drug-naïve (diet & exercise) or treated with diet and exercise plus metformin as monotherapy stable for >3 months before prescreening (1 week prior to screening visit). Only subjects treated with metformin monotherapy were eligible for the exenatide arm (consistent with labeling). Additional inclusion criteria included: BMI≥20 and ≤40 kg/m$^2$ and A1C at screening ≥7% and ≤10%.

Exclusion criteria included: any oral diabetes monotherapy (except metformin)≤3 months prior to screening or insulin <1 month prior to screening and not used for >7 days; pancreatitis <5 years; significant cardiovascular, cerebrovascular, renal or hepatobiliary disease; fasting serum triglycerides ≥800 mg/dL (9 mmol/L) at screening; and hematological profiles considered to be clinically significant. Subjects taking lipid-lowering medications must have been maintained at the same dose for 3 months prior to enrollment. Prescription or over-the-counter weight-loss drugs were not permitted.

The study protocol was approved by an Institutional Review Board and conducted in accordance with Good Clinical Practice and the Declaration of Helsinki Written informed consent was obtained from all subjects at prescreening. A Data Safety Monitoring Committee of independent experts assessed safety data on an ongoing basis.

Randomization

Subjects were randomized into 1 of 10 treatment arms: double-blind placebo (matched to albiglutide arms); albiglutide weekly (4, 15 or 30 mg), biweekly (15, 30 or 50 mg) or monthly (50 or 100 mg); or open-label exenatide (5 μg twice daily for 4 weeks followed by 12 weeks of 10 μg twice daily). Albiglutide and placebo were administered in the physician's office over the course of 16 weeks. Subjects receiving 4 mg albiglutide were given 1.0 mL (4 mg/mL solution). Subjects receiving 15 mg, 30 mg, or 50 mg albiglutide were given 0.32 mL, 0.65 mL, or 1.0 mL (50 mg/ml solution). Subjects receiving 100 mg albiglutide were given 2×1.0 mL injections (50 mg/mL solution, >1 inch apart). Placebo volumes were matched to active treatment. Albiglutide/placebo injections were subcutaneous to the abdomen using 30G needles. Subjects were observed for at ≥30 minutes to monitor for injection site reactions. Subjects receiving exenatide initiated treatment in the physician's office and subsequently self-administered according to the package insert. After 16 weeks, subjects entered an 11-week washout phase primarily to assess safety and immunogenicity.

Assessments
On-therapy:

A1C and fasting plasma glucose (FPG) measurements were performed at Screening, Baseline, and at Weeks 2 (FPG Only), 4, 5, 7, 8, 9, 12, 15, and 16. Fasting fructosamine, C-peptide, glucagon, insulin and lipids were measured at baseline and weeks 8, 12, and 16. β-cell function was calculated using homeostasis model assessment (HOMA) (Matthews, et al. *Diabetologia* 28:412-419, 1985).

Adverse event assessments and safety analyses (including electrocardiograms, vital sign measurements and physical exams) were conducted throughout the study. Nausea and vomiting were monitored for occurrence and duration. Immunogenicity assessments were performed with samples taken at baseline and at weeks 1, 4, 8, and 12, and 16. Samples were screened for anti-albiglutide antibodies via ELISA (Matthews, et al. *J Clin Endocrinol Metab.* 2008; DOI: 10.1210/jc.2008-1518). Plasma samples were collected to characterize the pharmacokinetics (PK) of albiglutide (quantified by ELISA at baseline and weeks 4, 5, 7, 8, 9, 12, 15, and 16). Population PK analysis was performed using a nonlinear mixed-effect modelling approach with NONMEM software (Icon Development Solutions, Ellicott City, Md.).

11-Week Washout:

Immunogenicity assessments were examined at weeks 20, 23, and 27; A1C and FPG were obtained at weeks 17, 18, 20, 23, and 27; fasting fructosamine, C-peptide, glucagon, insulin, and lipid profiles were obtained at weeks 20 and 27; and albiglutide concentrations were obtained at weeks 17, 18, 20, 23, and 27.

Statistical Analysis

The primary objective was to evaluate the dose response of albiglutide for safety and efficacy. With 30 subjects planned in each treatment arm, a 2-sided 95% confidence interval for each treatment group mean response had a half-width of 0.36% on the A1C measurement scale, assuming a standard deviation (SD) of 1.0%.

The primary efficacy endpoint was change from baseline A1C at week 16 vs placebo across different doses within each schedule (weekly, biweekly, and monthly). The primary analysis was an ANCOVA model with main effects for treatment group and prior metformin therapy, adjusting for baseline A1C. Dose response was evaluated using contrasts within the ANCOVA model framework. Pairwise comparisons were performed in the same ANCOVA model. Secondary endpoints were analyzed similarly. Responder analysis and incidence of hypoglycemia were summarized by group statistics. No formal statistical comparisons vs exenatide (open-label) were conducted. Safety and tolerability data were collected categorically.

Comparisons were made on the intent-to-treat population, defined as all randomly assigned subjects with at least one post-baseline assessment of the primary endpoint, using last-observation carried forward. The safety population included all randomized patients who received at least one dose of any medication after being randomized. An interim analysis was conducted at 8 weeks for administrative purposes by an independent statistical analysis group; blinding was retained for study investigators and study personnel with daily operational responsibility. No formal interim inferential hypothesis testing was conducted, the study was not terminated early, nor changed based on the result of the interim analysis.

Patients were also assessed for reduction in fasting plasma glucose (FPG) and HbA1c reduction based on background metformin (MET) treatment.

Results

Subject Disposition and Baseline Characteristics

A total of 774 subjects were screened. Of 361 subjects randomized, 356 (mean age 53 years, BMI 32.1 kg/m$^2$) received treatment and were included in the safety analysis; 345 subjects were included in the efficacy analysis, and 255 completed the 16-week trial. Withdrawal rates were similar across groups, the most frequent reasons for withdrawal were adverse events. The most frequent adverse events (occurring in >1 patient) leading to withdrawal included hyperglycemia (0-11.8%), gastrointestinal events (0-11.4%), events associated with injection site (0-9.7%) and hypertriglyceridemia (5.7%). Other reasons for withdrawal included loss to follow-up, protocol violations, and voluntary withdrawal.

Baseline demographics and characteristics were comparable across groups. Mean duration of diabetes was 5 years, and baseline A1C levels (mean 8.0%) were evenly distributed across arms. A similar proportion of subjects receiving placebo or albiglutide were drug-naïve (25.7-34.4%) or receiving metformin as monotherapy. All subjects receiving exenatide were on background metformin monotherapy. The groups were similar in terms of race and ethnicity (43.8-64.5% white; 87.1% and 12.9% of subjects were from US and Latin American clinics, respectively), fasting glucagon (range 94.4-108.9 ng/L), and rates of dyslipidemia, hypertension, and coronary artery disease (ranges: 50.0-80.0%; 47.1-67.6%; and 0-15.2%, respectively).

Efficacy

After 16 weeks, albiglutide significantly reduced A1C in a generally dose-dependent manner within each dose schedule (Table 1, FIG. 2A). Mean A1C reductions from baseline in subjects receiving highest dose in each treatment schedule were −0.87%, −0.79% and −0.87% for 30 mg weekly, 50 mg biweekly and 100 mg monthly, respectively, versus placebo (−0.17%) or exenatide (−0.54%). The A1C reductions (based on ANCOVA model) for the highest doses compared with placebo were statistically significant: 30 mg weekly −0.62% (95% CI −1.03, −0.22), P=0.003; 50 mg biweekly −0.57% (95% CI −0.96, −0.19), P=0.003; and 100 mg monthly −0.60% (95% CI, −0.99, −0.22) P=0.002. As expected, numerically greater reductions in A1C were observed in subjects with baseline A1C≥8.5%.

At week 16, A1C and FPG were reduced dose-dependently within all albiglutide dosing schedules. A1C was similarly reduced by albiglutide 30 mg weekly, 50 mg biweekly and 100 mg monthly (−0.9, −0.8 and −0.9%; respectively, p<0.005) vs PLACEBO (−0.2%). Results are summarized in Tables 1 and 2. HbA1c and American Diabetes Association glycemic target mean change from baseline are shown for all groups in FIG. 2 and FIG. 3.

TABLE 1

| | Dose (n) | A1C (%)[†] | FPG (mmol/L)[†] | A1C < 7.0% (%) |
|---|---|---|---|---|
| Placebo | (51) | −0.17 ± 1.0 | −0.10 ± 2.9 | 20 |
| Exenatide | 5/10 µg (35) | −0.5 ± 0.9 | −0.80 ± 2.5 | 35.3 |
| ALB weekly | 4 mg (35) | −0.1 ± 1.2 | −0.47 ± 3.1 | 17.6 |
| | 15 mg (35) | −0.5 ± 0.7 | −0.72 ± 1.7 | 35.3 |
| | 30 mg (31) | −0.9 ± 0.7* | −1.44 ± 2.0* | 51.7 |
| ALB biweekly | 15 mg (33) | −0.6 ± 1.0 | −1.28 ± 2.4 | 26.7 |
| | 30 mg (32) | −0.8 ± 1.0* | −1.58 ± 2.1* | 50.0 |
| | 50 mg (35) | −0.8 ± 1.0* | −1.32 ± 3.5* | 52.9 |
| ALB monthly | 50 mg (35) | −0.6 ± 1.0 | −0.72 ± 2.8 | 22.9 |
| | 100 mg (34) | −0.9 ± 0.9* | −1.22 ± 3.5* | 48.4 |

*p < .05 vs PBO;
[†]Mean ± SD (Δ From BL)

TABLE 2

Change from baseline in glycemic parameters at 16 weeks

| | | Exenatide[†] | Albiglutide | | | | | | | |
|---|---|---|---|---|---|---|---|---|---|---|
| | | Twice Daily | Weekly | | | Biweekly | | | Monthly | |
| | Placebo | 5 µg to 10 µg | 4 mg | 15 mg | 30 mg | 15 mg | 30 mg | 50 mg | 50 mg | 100 mg |
| N | 51 | 35 | 35 | 35 | 31 | 33 | 32 | 35 | 35 | 34 |
| Baseline A1C (%) Mean ± SD | 7.9 ± 0.9 | 7.9 ± 0.9 | 8.0 ± 1.0 | 8.1 ± 0.9 | 8.0 ± 0.9 | 8.2 ± 1.0 | 8.0 ± 1.0 | 8.0 ± 0.7 | 7.9 ± 0.8 | 8.6 ± 1.0 |
| ΔA1C at 16 weeks vs baseline, % ± SD | −0.17 ± 1.01 | −0.54 ± 0.91 | −0.11 ± 1.16 | −0.49 ± 0.74 | −0.87* ± 0.65 | −0.56 ± 0.97 | −0.79* ± 0.98 | −0.79* ± 1.04 | −0.55 ± 1.01 | −0.87* ± 0.87 |
| Baseline FPG, mmol/L ± SD | 10.0 ± 3.8 | 9.4 ± 2.4 | 10.8 ± 3.8 | 9.7 ± 2.9 | 9.5 ± 3.1 | 10.2 ± 2.7 | 9.5 ± 3.3 | 10.1 ± 3.2 | 9.3 ± 2.7 | 9.7 ± 3.8 |

TABLE 2-continued

Change from baseline in glycemic parameters at 16 weeks

|  | Placebo | Exenatide[†] Twice Daily 5 µg to 10 µg | Albiglutide Weekly | | | Biweekly | | | Monthly | |
| --- | --- | --- | --- | --- | --- | --- | --- | --- | --- | --- |
|  |  |  | 4 mg | 15 mg | 30 mg | 15 mg | 30 mg | 50 mg | 50 mg | 100 mg |
| ΔFPG at 16 weeks vs baseline, % ± SD | −0.10 ± 2.90 | −0.80 ± 2.48 | −0.47 ± 3.12 | −0.72 ± 1.68 | −1.44* ± 2.03 | −1.28 ± 2.43 | −1.58* ± 2.06 | −1.32* ± 3.52 | −0.72 ± 2.77 | −1.22* ± 3.50 |

FPG, fasting plasma glucose; A1C, glycosyluted hemoglobin; SD, standard deviation.
*p < 0.05 vs placebo
[†]Exenatide was used to provide clinical reference; no statistical analyses were conducted.

Weight loss (−0.9 to −1.8 kg) was observed with albiglutide. Documented hypoglycemia was not increased with albiglutide; most frequently reported AEs included nausea, vomiting and headache. Lowest incidence of gastrointestinal AEs was in those receiving weekly albiglutide 30 mg. No subject experienced pancreatitis. Most skin reactions were small and localized to injection site. Positive anti-ALB antibody occurred in 8 subjects (2.5%), including 1 on PLACEBO and 2 at baseline.

The proportion of subjects achieving ADA target for glycemic control (A1C<7.0%) at week 16 increased with increasing doses within each dose schedule; similar proportions of subjects achieved A1C targets at the highest albiglutide dose among the three schedules. Accordingly, more subjects receiving albiglutide 30 mg weekly (52%), 50 mg biweekly (53%), and 100 mg monthly (48%) achieved A1C<7.0%, compared with 20.0% and 35.3% of subjects receiving placebo and exenatide, respectively (FIG. 2B).

The time course of albiglutide-induced changes in FPG demonstrated that each dosing schedule of albiglutide elicited a dose-dependent reduction in FPG over 16 weeks, with no changes in FPG observed in subjects receiving placebo. Rapid reductions in FPG were observed, with FPG reduction at the 16-week endpoint similar for each of the highest doses (FIG. 3C). Statistically significant reductions were seen for FPG changes from baseline compared with placebo at week 16 [−1.38 (P=0.01), −1.16 (P=0.03), and −1.17 (P=0.02) mmol/L for 30 mg albiglutide weekly, 50 mg biweekly and 100 mg monthly doses, respectively]. The 4 mg and 15 mg weekly dose regimens of albiglutide reduced FPG but were less effective. Notably, the greatest fluctuations in FPG over time were observed in subjects receiving the monthly dosing regimen (FIG. 3C). Exenatide was associated with a relatively consistent FPG profile over time that was numerically less than FPG reductions seen with the highest doses of albiglutide (FIG. 3C).

Neither fasting insulin nor glucagon levels were consistently or significantly altered. Small improvements in β-cell function (assessed by HOMA-B) were noted in subjects receiving albiglutide.

There was no significant difference in weight reduction among groups. A consistent trend in weight reduction was noted, with average weight loss ranging from −1.1 to −1.7 kg in subjects receiving albiglutide at the highest dose regimens in each timing schedule. These reductions were numerically greater than those receiving placebo (−0.7 kg), but less than weight loss with exenatide (−2.4 kg). Albiglutide and exenatide tended to reduce mean systolic and diastolic blood pressure, but did not significantly change the plasma lipoprotein profile.

Across albiglutide groups and placebo, 65.6-74.3% received background metformin (MET). After 16 weeks, background MET subjects experienced fasting plasma glucose (FPG) reductions of −1.26, −2.10, −1.80 and −0.07 mmol/L for the 30 mg weekly, 50 mg biweekly and 100 mg monthly doses of albiglutide and placebo, respectively, vs −1.44, −1.32, −1.22 and −0.10 mmol/L, respectively, for the overall population. Exenatide decreased FPG by −0.80 mmol/L.

In MET subjects, the highest albiglutide doses in each dose schedule significantly reduced HbA1c similarly over 16 weeks: albiglutide 30 mg weekly, −0.78%; albiglutide 50 mg biweekly −0.83%; and albiglutide 100 mg monthly −0.77% vs placebo (−0.05%, p<0.05); exenatide reduced HbA1c by −0.54%. In the overall population, HbA1c was reduced −0.87, −0.79 and −0.87% by albiglutide 30 mg weekly, 50 mg biweekly and 100 mg monthly dosing, respectively, vs placebo (−0.17%, p<0.005).

Among MET patients, HbA1c <7% was achieved by 43%, 50% and 46% of subjects receiving albiglutide 30 mg weekly, 50 mg biweekly and 100 mg monthly, respectively, vs 15% with placebo and 35% in the exenatide group. Weight loss with albiglutide was observed in both the MET group (−0.4 to −2.1 kg) and in the overall population (−0.9 to −1.8 kg). Documented hypoglycaemia was not increased with albiglutide, and most commonly reported AEs were gastrointestinal events. Rates of nausea or vomiting in MET subjects were 18.2%, 47.8% and 56.5% of patients receiving 30 mg weekly, 50 mg biweekly and 100 mg monthly doses of albiglutide, respectively, vs 29.0%, 54.3% and 55.9% in the overall study population. Nausea or vomiting was experienced by 45.7% in the exenatide group.

Safety and Tolerability

The percentage of patients reporting at least 1 adverse event was similar across groups (67-85%). The most frequently reported adverse events included nausea (11.8-54.3%), vomiting (0-41.2%), headache (5.9-23.5%), dizziness (5.7-14.3%), nasopharyngitis (5.7-11.4%), back pain (0-14.3%), influenza (0-9.7%), upper respiratory tract infections (0-15.2%), and local skin reactions (2.9-28.6%).

The proportion of subjects who experienced nausea and/or vomiting was lower with administration of ≤30 mg albiglutide compared with the proportion of subjects receiving higher doses (within other dose regimens). In the 30 mg weekly arm, 29.0% of subjects experienced nausea and/or vomiting, compared with 54.3% of subjects in the 50 mg biweekly group and 55.9% of patients in the 100 mg monthly group. The percentage of exenatide patients who experienced nausea and/or vomiting also was numerically higher (45.7%) than was seen in the 30 mg weekly albiglutide groups.

Examination of the time course (FIG. 4) of nausea and/or vomiting revealed that the proportion of subjects experiencing nausea and/or vomiting each week was low in the 30 mg weekly arm (<10%), and declined over the course of the study, with no reports of nausea or vomiting after 8 weeks (FIG. 4C). Although the proportion of nausea and/or vomiting in patients receiving the albiglutide 50 mg biweekly dose was greater than in subjects receiving albiglutide 30 mg weekly, the incidence of these adverse events also declined over the study period (FIG. 4D). Subjects receiving the 100 mg monthly dose of albiglutide also experienced higher rates of nausea and/or vomiting, with peak incidence occurring following each monthly dose administration. The overall rate was higher for 100 mg monthly than for any other albiglutide group (FIG. 4E). The incidence of nausea and/or vomiting with exenatide reached 20% by week 2, incidence increased at week 5 to a peak incidence of 29% (due to label-based titration) and also declined over the study period (FIG. 4B).

Other adverse events were less common than GI-related events and were similar across groups, with no dose-dependent trends. Documented hypoglycemia was not increased with albiglutide (0-3.1%) relative to placebo (3.9%) and exenatide (2.9%). Cardiac-related adverse events (8 subjects) were distributed across groups with no dose-dependent trends. No episodes of pancreatitis were reported.

An 11-week post-treatment washout period was included to monitor development of anti-albiglutide antibodies. A total of eight (2.5%) subjects confirmed positive at least once for anti-albiglutide antibodies in the placebo and albiglutide arms after their baseline measurement. However, 2 subjects tested positive prior to albiglutide treatment (1 each in the 4 mg weekly and 15 mg weekly arms) and 1 subject received placebo. The remaining 5 albiglutide-positive subjects were detected in the albiglutide weekly and biweekly arms. The appearance of anti-albiglutide antibodies was largely transient, with 1 subject remaining positive at week 27. Antibodies were non-neutralizing, low-titer, and in 4 of the 5 subjects showed cross-reactivity with GLP-1. There was no obvious association between presence of anti-albiglutide antibodies and either efficacy or safety.

Injection site local skin reactions were observed in the study, most of which were small, localized to injection site, and were more common in the albiglutide groups (2.9-28.2%) compared with placebo (5.9%) and exenatide (2.9%). Injection site reactions tended to occur once/person in subjects receiving 30 mg albiglutide doses, and approximately twice/person in subjects receiving higher albiglutide doses. None of the skin reactions was associated with positive IgE antibodies or neutralizing antibodies. The skin reactions did not worsen upon repeated dosing and did not appear to be dose related. No systemic allergic reactions attributable to albiglutide were observed.

Pharmacokinetics

Albiglutide exhibited a half-life of ~5 days. Steady state levels of albiglutide were reached within ~4-5 weeks of the first dose. Greater peak/trough fluctuations in circulating albiglutide concentrations were observed with the less-frequent administration of higher albiglutide doses.

Conclusions

In this study, the dose- and time-dependent effects of albiglutide, a long-acting GLP-1 receptor agonist, were evaluated to identify potential dose regimens for future studies. Within each dose schedule, albiglutide appeared to be associated with dose-dependent A1C reductions that were significantly different from placebo. Maximum doses used for each schedule (albiglutide 30 mg weekly, 50 mg biweekly, and 100 mg monthly) elicited similar responses in A1C, providing meaningful reductions within the range ~0.8-0.9% from a mean baseline A1C of 8.0%.

Albiglutide also significantly reduced FPG at week 16 compared with placebo. FPG reductions were observed at the time of the first assessment (2 weeks post-dose). In a previous study, FPG reductions were observed as early as 2 days following a single dose.

Variability in glycemic response appeared to be related to circulating concentrations of albiglutide. With a half-life of ~5 days and at doses sufficient to achieve consistent therapeutic response (i.e., 30 mg), weekly dosing provided consistent FPG reduction; greater fluctuations in FPG were observed following biweekly or monthly dosing despite similar A1C reductions.

Albiglutide 30 mg weekly dosing elicited steady and consistent improvement in FPG reductions with a nausea and vomiting profile more favorable than the reference comparator, exenatide. When dosed biweekly, 50 mg albiglutide also improved glycemic indices, but with higher GI adverse event rates possibly related to the higher initial dose. In all dosing schedules, rates of nausea and vomiting declined over time. An escalating-dose titration for the biweekly regimen might have resulted in a lower frequency of GI events and will be tested in future studies. However, when dosed monthly, albiglutide (50 or 100 mg) did not appear to produce stable FPG reductions between dosing and was associated with higher GI event rates. The increase in FPG fluctuation and GI events in the biweekly and monthly regimens were most likely due to fluctuations in albiglutide concentrations resulting from less-frequent dosing. Taken together, the efficacy and safety profile in this study suggests that weekly dosing with at least 30 mg albiglutide provides rapid and sustained glycemic control accompanied by favorable GI tolerability. Future studies may be designed to investigate whether a biweekly schedule could be an attractive maintenance option for patients who respond and tolerate the initial weekly regimen.

Mechanistically, reasons for differences in the tolerability profile of albiglutide and exenatide are unknown but may be due to differences in pharmacokinetics ($T_{max}$ is ~3 days vs 2.1 hours for albiglutide and exenatide, respectively) that result in a long half-life of ~5 days and a steady state achieved after 4-5 doses for 30 mg albiglutide weekly. The slow accumulation of albiglutide may ameliorate the GI intolerability often observed with short-acting GLP-1 mimetics. In addition, since albiglutide is relatively impermeant to the central nervous system (Baggio, et al. *Diabetes* 53:2492-2500, 2004), it may have a more benign profile with respect to nausea and vomiting than does exenatide.

Weight loss was similar across albiglutide arms and numerically less than the exenatide reference arm. However, larger, longer-term studies are needed to determine the true effect on weight and cardiometabolic parameters.

Immunogenicity of albiglutide was closely monitored owing to the possible appearance of neutralizing antibodies or development of immediate hypersensitivity reactions. In the present study, anti-albiglutide antibodies were detected in 2.5% (n=8) of subjects. However, the observation that positive titers of anti-albiglutide antibodies were detected in 2 subjects at baseline suggests that the immunogenicity rate may be overestimated. Exenatide, which has ~50% homology to human GLP-1, (Drucker, et al. *Proc Natl Acad Sci USA* 84:3434-3438, 1987) is associated with treatment-emergent antibody development following administration with twice-daily (DeFronzo, et al. *Diabetes Care* 28:1092-1100, 2005; Kendall, et al. *Diabetes Care* 28:1083-1091, 2005; Zinman, et al. *Ann Intern Med* 146:477-485, 2007; Buse, et al. *Diabetes Care* 27:2628-2635, 2004) and weekly (Drucker, et al. *Lancet* 372:1240-1250, 2008) formulations (>40%). Antibody formation may attenuate efficacy, especially among patients developing high levels of anti-exenatide antibodies (Drucker, et al. *Lancet* 372:1240-1250, 2008).

There are limitations of this phase 2 dose- and schedule-finding study. First, the number of patients in each arm is relatively small compared with phase 3 studies. Second, relative to the total number of subjects, the drop-out rate was high, due to adverse events, loss to follow-up, and voluntary withdrawals. Third, the duration of active treatment was 16 weeks, so full appreciation of the magnitude or durability of response cannot be determined. Finally, no escalating doses were tested for biweekly and monthly dosing that may have attenuated the frequency of GI adverse events and fluctuating FPG response.

In summary, albiglutide improves glucose control in a dose-dependent manner when given weekly and biweekly. Higher monthly doses of albiglutide are efficacious, but their use is constrained by the higher frequency of GI-related adverse events. In conclusion, albiglutide administered weekly significantly improved glycemic control vs placebo, with an acceptable safety and tolerability profile, modest weight loss, and without increasing the risk of hypoglycemia or immunological response in subjects with type 2 diabetes. In conclusion, weekly albiglutide significantly improved glycemic control with a favorable safety and tolerability profile; biweekly albiglutide may have potential as a maintenance option in patients with T2DM.

Albiglutide was effective in patients receiving background MET and provided numerically greater HbA1c and FPG reductions than did exenatide. Tolerability was most favourable with the 30 mg weekly albiglutide group.

Example 2

Gastrointestinal Adverse Event Profile of Albiglutide in Subjects with Type 2 Diabetes Gastrointestinal (GI) adverse events may limit adherence to GLP-1 therapies. The time course of nausea and vomiting (N&V) was assessed in a 16-week randomized, multicenter, double-blind, parallel-group study; 356 subjects with type 2 diabetes (T2D) received placebo (PBO), albiglutide (ALB) [weekly (4, 15 or 30 mg), biweekly (15, 30 or 50 mg) or monthly (50 or 100 mg)] or exenatide (Ex, open label) over 16 wks. Combined incidence of N&V in placebo and exenatide was 11.8% and 45.7%, respectively. Combined incidence of N&V was reported by 29%, 54.3% and 55.9% of subjects receiving albiglutide 30 mg weekly, 50 mg biweekly and 100 mg monthly (mean duration: 2.3, 3.3 and 5.8d). Incidence of N&V was lower with more-frequent, smaller albiglutide doses vs less-frequent higher albiglutide doses. All 30 mg weekly events were mild; >90% of 50 mg biweekly or 100 mg monthly were mild/moderate. N&V correlated with albiglutide exposure, and decreased over time. N&V are summarized in Table 3 below.

TABLE 3

| Week | PBO | Exenatide | ALB 30 mg weekly | ALB 50 mg biweekly | ALB 100 mg monthly |
|---|---|---|---|---|---|
| 1 | 2/0 | 14.3/2.9 | 6.5/3.2 | 25.7/5.7 | 29.4/17.6 |
| 2 | 3.9/0 | 20/5.7 | 6.5/0 | 12.1/0 | 15.2/3 |
| 3 | 0/0 | 15.2/3 | 9.7/3.2 | 18.2/6.1 | 6.3/3.1 |
| 4 | 2/0 | 12.5/3.1 | 6.7/0 | 3/0 | 3.1/3.1 |
| 5 | 2/0 | 29/9.7 | 3.3/3.3 | 21.9/9.4 | 41.9/22.6 |
| 6 | 0/0 | 29/6.5 | 6.9/0 | 6.3/3.1 | 6.5/3.2 |
| 7 | 0/0 | 25.8/6.5 | 6.9/3.4 | 12.5/6.3 | 3.2/3.2 |
| 8 | 0/0 | 19.4/0 | 3.4/3.4 | 12.9/3.2 | 3.2/3.2 |
| 9 | 2.1/2.1 | 16.1/0 | 0/0 | 16.1/6.5 | 25.8/19.4 |
| 10 | 0/0 | 19.4/3.2 | 0/0 | 10.3/0 | 6.9/3.4 |
| 11 | 0/0 | 6.5/0 | 0/0 | 7.7/0 | 7.1/3.6 |
| 12 | 0/0 | 6.5/0 | 0/0 | 4/4 | 3.7/3.7 |
| 13 | 0/0 | 6.5/0 | 0/0 | 8/8 | 18.5/11.1 |
| 14 | 2.3/0 | 3.2/0 | 0/0 | 4/0 | 0/0 |
| 15 | 2.4/0 | 3.2/0 | 0/0 | 0/0 | 0/0 |
| 16 | 0/0 | 0/0 | 0/0 | 0/0 | 0/0 |

Data = N&V/vomiting alone, %

FIG. 4 shows a "Time Course of Nausea and Vomiting as Adverse Events." The percentage of subjects experiencing vomiting with or without nausea (gray bars) or nausea (white bars) adverse events during each week of the 16 Week trial is shown for A) placebo, B) exenatide, C) albiglutide 30 mg weekly, D) albiglutide 50 mg biweekly and E) albiglutide 100 mg monthly.

In conclusion, weekly 30 mg albiglutide shows a favorable N&V profile vs other albiglutide regimens and Exenatide.

Example 3

Safety, Pharmacokinetics and Pharmacodynamics of Albiglutide in Japanese Subjects With Type 2 Diabetes A Phase III Study Albiglutide (ALB) is a long-acting GLP-1 mimetic shown to improve indices of glycemia in Caucasian/Hispanic populations when dosed weekly, once every other week (biweekly) and monthly. Pharmacokinetics, pharmacodynamics and safety/tolerability of albiglutide in Japanese subjects with type 2 diabetes (T2D) were assessed in this 28 day, single-blind, randomized, placebo (PBO)-controlled study; 40 subjects (mean 54.5y, BMI 24.5 kg/m$^2$, A1C range 6.3-10.3%) were given (sc, abdomen) albiglutide: 15 mg or 30 mg once-weekly; 50 mg biweekly; or 100 mg monthly. Albiglutide was generally well-tolerated; GI events were comparable to placebo in all doses except 100 mg monthly and were numerically lowest in the 30 mg weekly group. In the 100 mg monthly group, most common AEs were flatulence (n=3, 38%), vomiting (n=3, 38%) and nausea (n=2, 25%). No serious AEs were reported. Albiglutide had a plasma t1/2 of 5.3d, CL/F of 68.7 mL/hr, and V/F of 12.6L. FPG and weighted mean AUC0-4 glucose were improved as early as day 3. At week 29, all doses of albiglutide except 100 mg monthly dose showed a significant change from baseline compared with PLACEBO for FPG and AUC0-4 glucose. Albiglutide also significantly reduced A1C at all doses on day 29 and 43. Results are summarized in Table 4 below.

TABLE 4

| | Albiglutide Dose | | | |
|---|---|---|---|---|
| PBO-adjusted change from baseline (LS Means Difference) | 15 mg weekly (n = 8) | 30 mg weekly (n = 8) | 50 mg biweekly (n = 8) | 100 mg monthly (n = 8) |
| FPG, mg/dL (day 29) | −34.5* | −35.6* | −31.3* | −13.2 |
| AUC$_{0-4}$ glucose, mg/mL(day 29) | −51.6* | −64.5* | −45.2* | −25.9 |
| A1C, % (day 29/43) | −0.58*/ −0.87* | −0.57*/ −0.78* | −0.63*/ −0.79* | −0.51*/ −0.59* |

*P < .05 vs PBO

In conclusion, weekly/biweekly albiglutide significantly improved glycemic control with a favorable safety and tolerability profile in Japanese subjects with T2D.

Example 4

Albiglutide Administered in Combination with Insulin Glargine

Albiglutide is administered as a weekly subcutaneously injected dose of albiglutide in combination with insulin glargine as compared with the combination of insulin glargine and preprandial lispro insulin in subjects with type 2 diabetes. Subjects with a historical diagnosis of type 2 diabetes who are inadequately controlled despite the use of insulin glargine or other intermediate- or long-acting insulins for >/=6 months but <5 years, with or without oral antidiabetic medications, who are unable to achieve a glycosylated hemoglobin value of <7% will be recruited into the study. Subjects must also be willing and capable of pursuing an intensive regimen of both basal and preprandial insulin.

---

The invention claimed is:

1. A pharmaceutical composition comprising a polypeptide consisting of the amino acid sequence set forth in SEQ ID NO:1 wherein an effective dose of said pharmaceutical composition comprises 30 mg of said polypeptide.

* * * * *

SEQUENCE LISTING

<160> NUMBER OF SEQ ID NOS: 2

<210> SEQ ID NO 1
<211> LENGTH: 645
<212> TYPE: PRT
<213> ORGANISM: Homo Sapiens

<400> SEQUENCE: 1

```
His Gly Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg His Gly
                20                  25                  30

Glu Gly Thr Phe Thr Ser Asp Val Ser Ser Tyr Leu Glu Gly Gln Ala
            35                  40                  45

Ala Lys Glu Phe Ile Ala Trp Leu Val Lys Gly Arg Asp Ala His Lys
        50                  55                  60

Ser Glu Val Ala His Arg Phe Lys Asp Leu Gly Glu Glu Asn Phe Lys
65                  70                  75                  80

Ala Leu Val Leu Ile Ala Phe Ala Gln Tyr Leu Gln Gln Cys Pro Phe
                85                  90                  95

Glu Asp His Val Lys Leu Val Asn Glu Val Thr Glu Phe Ala Lys Thr
                100                 105                 110

Cys Val Ala Asp Glu Ser Ala Glu Asn Cys Asp Lys Ser Leu His Thr
            115                 120                 125

Leu Phe Gly Asp Lys Leu Cys Thr Val Ala Thr Leu Arg Glu Thr Tyr
    130                 135                 140

Gly Glu Met Ala Asp Cys Cys Ala Lys Gln Glu Pro Glu Arg Asn Glu
145                 150                 155                 160

Cys Phe Leu Gln His Lys Asp Asp Asn Pro Asn Leu Pro Arg Leu Val
                165                 170                 175

Arg Pro Glu Val Asp Val Met Cys Thr Ala Phe His Asp Asn Glu Glu
                180                 185                 190

Thr Phe Leu Lys Lys Tyr Leu Tyr Glu Ile Ala Arg Arg His Pro Tyr
            195                 200                 205

Phe Tyr Ala Pro Glu Leu Leu Phe Phe Ala Lys Arg Tyr Lys Ala Ala
        210                 215                 220

Phe Thr Glu Cys Cys Gln Ala Ala Asp Lys Ala Ala Cys Leu Leu Pro
225                 230                 235                 240

Lys Leu Asp Glu Leu Arg Asp Glu Gly Lys Ala Ser Ser Ala Lys Gln
                245                 250                 255

Arg Leu Lys Cys Ala Ser Leu Gln Lys Phe Gly Glu Arg Ala Phe Lys
                260                 265                 270

Ala Trp Ala Val Ala Arg Leu Ser Gln Arg Phe Pro Lys Ala Glu Phe
            275                 280                 285
```

-continued

```
Ala Glu Val Ser Lys Leu Val Thr Asp Leu Thr Lys Val His Thr Glu
        290                 295                 300
Cys Cys His Gly Asp Leu Leu Glu Cys Ala Asp Asp Arg Ala Asp Leu
305                 310                 315                 320
Ala Lys Tyr Ile Cys Glu Asn Gln Asp Ser Ile Ser Ser Lys Leu Lys
                325                 330                 335
Glu Cys Cys Glu Lys Pro Leu Leu Glu Lys Ser His Cys Ile Ala Glu
            340                 345                 350
Val Glu Asn Asp Glu Met Pro Ala Asp Leu Pro Ser Leu Ala Ala Asp
        355                 360                 365
Phe Val Glu Ser Lys Asp Val Cys Lys Asn Tyr Ala Glu Ala Lys Asp
370                 375                 380
Val Phe Leu Gly Met Phe Leu Tyr Glu Tyr Ala Arg Arg His Pro Asp
385                 390                 395                 400
Tyr Ser Val Val Leu Leu Leu Arg Leu Ala Lys Thr Tyr Glu Thr Thr
                405                 410                 415
Leu Glu Lys Cys Cys Ala Ala Ala Asp Pro His Glu Cys Tyr Ala Lys
            420                 425                 430
Val Phe Asp Glu Phe Lys Pro Leu Val Glu Glu Pro Gln Asn Leu Ile
        435                 440                 445
Lys Gln Asn Cys Glu Leu Phe Glu Gln Leu Gly Glu Tyr Lys Phe Gln
450                 455                 460
Asn Ala Leu Leu Val Arg Tyr Thr Lys Lys Val Pro Gln Val Ser Thr
465                 470                 475                 480
Pro Thr Leu Val Glu Val Ser Arg Asn Leu Gly Lys Val Gly Ser Lys
                485                 490                 495
Cys Cys Lys His Pro Glu Ala Lys Arg Met Pro Cys Ala Glu Asp Tyr
            500                 505                 510
Leu Ser Val Val Leu Asn Gln Leu Cys Val Leu His Glu Lys Thr Pro
        515                 520                 525
Val Ser Asp Arg Val Thr Lys Cys Cys Thr Glu Ser Leu Val Asn Arg
530                 535                 540
Arg Pro Cys Phe Ser Ala Leu Glu Val Asp Glu Thr Tyr Val Pro Lys
545                 550                 555                 560
Glu Phe Asn Ala Glu Thr Phe Thr Phe His Ala Asp Ile Cys Thr Leu
                565                 570                 575
Ser Glu Lys Glu Arg Gln Ile Lys Lys Gln Thr Ala Leu Val Glu Leu
            580                 585                 590
Val Lys His Lys Pro Lys Ala Thr Lys Glu Gln Leu Lys Ala Val Met
        595                 600                 605
Asp Asp Phe Ala Ala Phe Val Glu Lys Cys Cys Lys Ala Asp Asp Lys
610                 615                 620
Glu Thr Cys Phe Ala Glu Glu Gly Lys Lys Leu Val Ala Ala Ser Gln
625                 630                 635                 640
Ala Ala Leu Gly Leu
                645

<210> SEQ ID NO 2
<211> LENGTH: 31
<212> TYPE: PRT
<213> ORGANISM: Homo Sapiens
<220> FEATURE:
<221> NAME/KEY: VARIANT
<222> LOCATION: 31
<223> OTHER INFORMATION: Xaa = Any Amino Acid

<400> SEQUENCE: 2
```

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Xaa
                20                  25                  30
```